(12) United States Patent
Laskowitz et al.

(10) Patent No.: US 9,018,169 B2
(45) Date of Patent: Apr. 28, 2015

(54) PEPTIDES FOR SUPPRESSING INFLAMMATION

(75) Inventors: Daniel T. Laskowitz, Chapel Hill, NC (US); Hana Dawson, Cary, NC (US); Brad Kolls, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/981,238

(22) PCT Filed: Mar. 16, 2012

(86) PCT No.: PCT/US2012/029392
§ 371 (c)(1),
(2), (4) Date: Oct. 15, 2013

(87) PCT Pub. No.: WO2012/129077
PCT Pub. Date: Sep. 27, 2012

(65) Prior Publication Data
US 2014/0038898 A1 Feb. 6, 2014

Related U.S. Application Data

(60) Provisional application No. 61/454,342, filed on Mar. 18, 2011.

(51) Int. Cl.
*A61K 38/00* (2006.01)
*C07K 7/06* (2006.01)
*C07K 14/775* (2006.01)

(52) U.S. Cl.
CPC . *C07K 7/06* (2013.01); *A61K 38/00* (2013.01); *C07K 14/775* (2013.01)

(58) Field of Classification Search
None
See application file for complete search history.

(56) References Cited

U.S. PATENT DOCUMENTS

| | | | |
|---|---|---|---|
| 7,329,638 B2 | 2/2008 | Yang et al. | |
| 7,482,328 B2 | 1/2009 | Yoshida et al. | |
| 8,377,651 B2 | 2/2013 | Colpas et al. | |
| 8,394,390 B2 | 3/2013 | Galeotti et al. | |
| 2003/0072794 A1 | 4/2003 | Boulikas | |
| 2004/0121443 A1 | 6/2004 | Carr et al. | |
| 2005/0042753 A1 | 2/2005 | Yang et al. | |
| 2006/0205646 A1 | 9/2006 | Sanders et al. | |
| 2006/0234909 A1 | 10/2006 | Newman et al. | |
| 2007/0196881 A1 | 8/2007 | Colpas et al. | |
| 2007/0269851 A1 | 11/2007 | Sanders et al. | |
| 2009/0304778 A1 | 12/2009 | Sanders et al. | |
| 2011/0236429 A1 | 9/2011 | Hancock et al. | |

FOREIGN PATENT DOCUMENTS

| | | |
|---|---|---|
| WO | WO 01/31019 A2 | 5/2001 |
| WO | WO 02/069997 A1 | 9/2002 |
| WO | WO 03/026479 A2 | 4/2003 |
| WO | WO 03/026479 A3 | 4/2003 |
| WO | WO 2004/087942 A2 | 10/2004 |
| WO | WO 2005/004894 A2 | 1/2005 |
| WO | WO 2005/021780 A1 | 3/2005 |
| WO | WO 2005/035003 A2 | 4/2005 |
| WO | WO 2005/042771 A2 | 5/2005 |
| WO | WO 2007/092360 A2 | 8/2007 |
| WO | WO 2007/092909 A2 | 8/2007 |
| WO | WO 2008/022444 A1 | 2/2008 |
| WO | WO 2009/028943 A1 | 3/2009 |
| WO | WO 2013/034982 A2 | 3/2013 |

OTHER PUBLICATIONS

Vlieghe P et al. Synthetic therapeutic peptides: science and market. Drug Discovery Today. Jan. 2010; 15(1/2): 40-56.
International Search Report and Written Opinion, PCT/US2012/029392, mailed Sep. 7, 2013.
Partial Supplementary European Search Report Corresponding to European Patent Application No. 12 76 0270; Dated: Feb. 2, 2015; 7 Pages.
Boulikas, T. "Nucleocytoplasmic trafficking: implications for the nuclear import of plasmid DNA during gene therapy", *Gene Therapy and Molecular Biology Gene Ther Mol Biol*, vol. 1, Mar. 1998, pp. 713-741.
Li-Chien Chang et al. "Low molecular weight protamine as nontoxic heparin/low molecular weight heparin antidote (III): Preliminary in vivo evaluation of efficacy and toxicity using a canine model", *AAPS Pharmsci*, vol. 3, No. 2, Sep. 1, 2001, 8 Pages.
Matusik et al. "Regulation of Gene Expression in the Prostate", *Molecular and Cellular Biology of Prostate Cancer*, Jan. 1, 1991, 299-314.
Wang et al. "An apolipoprotein E-based therapeutic improves outcome and reduces Alzheimer's disease pathology following closed head injury: Evidence of pharmacogenomic interaction" *Neuroscience*, vol. 144, No. 4, Jan. 24, 2007, 1324-1333.

*Primary Examiner* — John Ulm
(74) *Attorney, Agent, or Firm* — Myers Bigel Sibley & Sajovec, P.A.

(57) ABSTRACT

Provided herein are peptides that exhibit ApoE biological activity, as well as compositions and pharmaceutical formulations that include the peptides. The peptides, compositions, and methods disclosed herein have broad applications as they can be used to treat a broad spectrum of injury, diseases, disorders, and clinical indications.

12 Claims, 12 Drawing Sheets

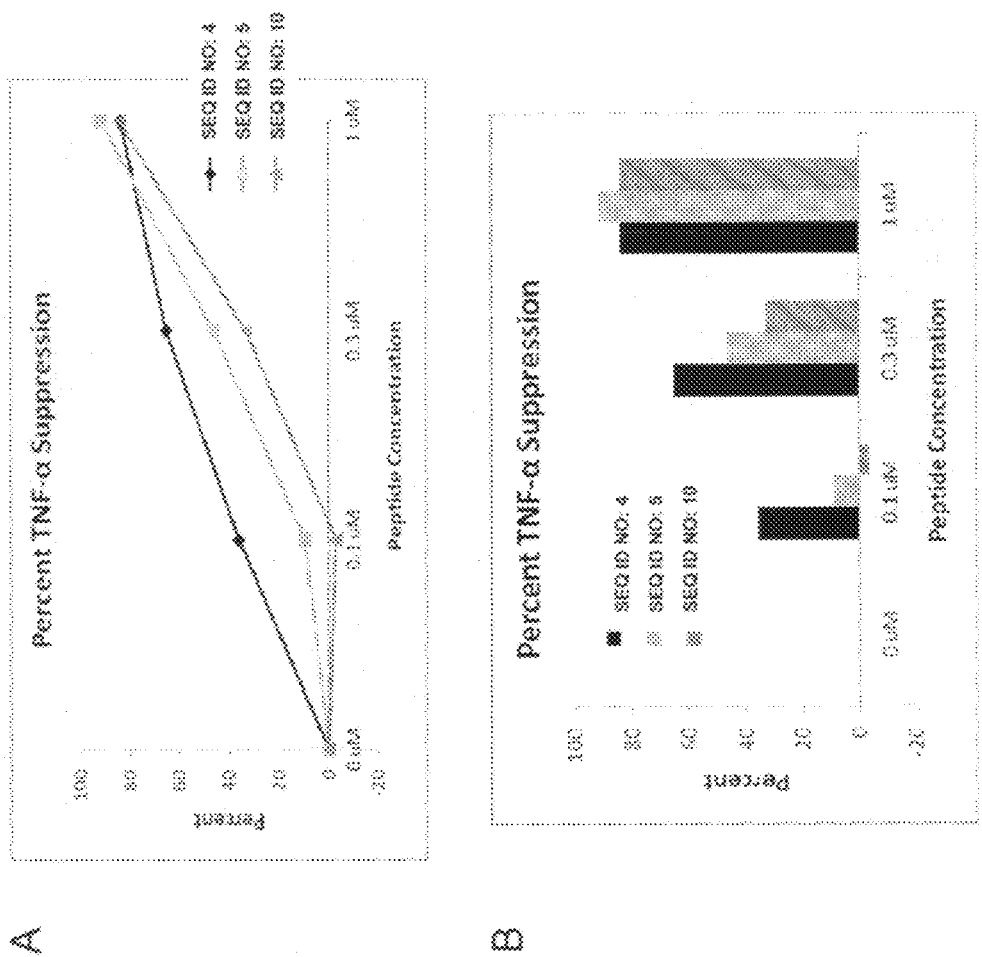

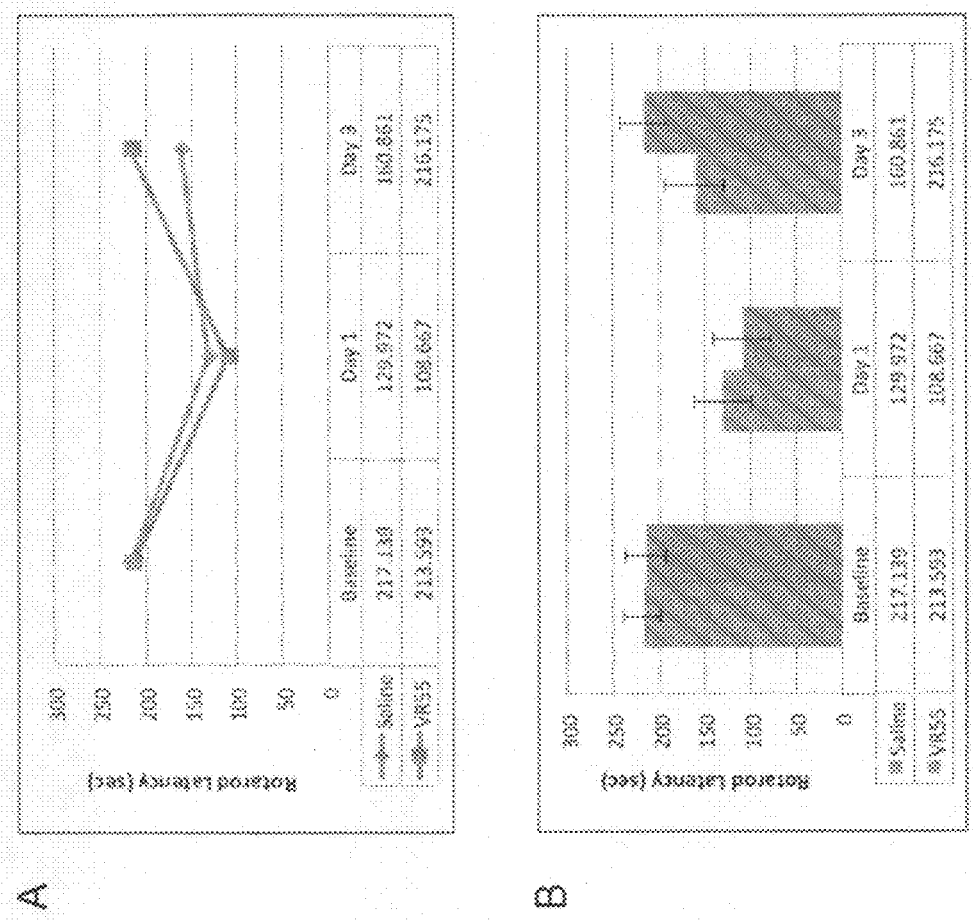

SEQUENCE LISTING

<160> NUMBER OF SEQ ID NOS: 19

<210> SEQ ID NO 1
<211> LENGTH: 5
<212> TYPE: PRT
<213> ORGANISM: Artificial
<220> FEATURE:
<223> OTHER INFORMATION: ApoE mimetic anti-inflammatory peptide sequence
<220> FEATURE:
<221> NAME/KEY: MISC_FEATURE
<222> LOCATION: (1)..(1)
<223> OTHER INFORMATION: Xaa can be an amino acid having a hydrophobic
      side chain or an amino acid having a positively charged side
      chain
<220> FEATURE:
<221> NAME/KEY: MISC_FEATURE
<222> LOCATION: (2)..(2)
<223> OTHER INFORMATION: Xaa can be an amino acid having a hydrophobic
      side chain, an amino acid having a positively charged side chain,
      or an amino acid having a polar uncharged side chain
<220> FEATURE:
<221> NAME/KEY: MISC_FEATURE
<222> LOCATION: (3)..(4)
<223> OTHER INFORMATION: Xaa can be an amino acid having a positively
      charged side chain
<220> FEATURE:
<221> NAME/KEY: MISC_FEATURE
<222> LOCATION: (5)..(5)
<223> OTHER INFORMATION: Xaa can be an amino acid having a hydrophobic
      side chain or an amino acid having a positively charged side chain

<400> SEQUENCE: 1

Xaa Xaa Xaa Xaa Xaa
1               5

<210> SEQ ID NO 2
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 2

Val Ser Arg Lys Arg
1               5

<210> SEQ ID NO 3
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 3

Val Ser Lys Arg Arg
1               5

<210> SEQ ID NO 4
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 4

Val Ser Arg Arg Arg
1               5

<210> SEQ ID NO 5
<211> LENGTH: 5

```
<212> TYPE: PRT
<213> ORGANISM: Artificial
<220> FEATURE:
<223> OTHER INFORMATION: ApoE mimetic peptide sequence

<400> SEQUENCE: 5

Val Ala Arg Lys Leu
1               5

<210> SEQ ID NO 6
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 6

Arg His Lys Lys Leu
1               5

<210> SEQ ID NO 7
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 7

Arg Ala Arg Arg Leu
1               5

<210> SEQ ID NO 8
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 8

Arg Ser Lys Lys Leu
1               5

<210> SEQ ID NO 9
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 9

Arg His Lys Arg Arg
1               5

<210> SEQ ID NO 10
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 10

Val Ala Arg Arg Leu
1               5

<210> SEQ ID NO 11
<211> LENGTH: 5
<212> TYPE: PRT
```

```
<213> ORGANISM: Artificial
<220> FEATURE:
<223> OTHER INFORMATION: ApoE mimetic peptide sequence

<400> SEQUENCE: 11

Val Ala Arg Arg Lys
1               5

<210> SEQ ID NO 12
<211> LENGTH: 5
<212> TYPE: PRT
<213> ORGANISM: Artificial
<220> FEATURE:
<223> OTHER INFORMATION: ApoE mimetic peptide sequence

<400> SEQUENCE: 12

Arg Ser Lys Arg Arg
1               5

<210> SEQ ID NO 13
<211> LENGTH: 5
<212> TYPE: PRT
<213> ORGANISM: Artificial
<220> FEATURE:
<223> OTHER INFORMATION: Synthetic negative control peptide sequence

<400> SEQUENCE: 13

Val Ser Lys Lys Arg
1               5

<210> SEQ ID NO 14
<211> LENGTH: 299
<212> TYPE: PRT
<213> ORGANISM: Homo sapiens

<400> SEQUENCE: 14

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190
```

```
Ala Thr Val Gly Ser Leu Ala Gly Gln Pro Leu Gln Glu Arg Ala Gln
            195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Ala Gln Ala Arg Leu Lys Ser Arg Phe Glu Pro Leu Ala Glu Asp Met
            260                 265                 270

Gln Arg Gln Trp Ala Gly Gln Val Glu Lys Val Gln Ala Ala Glu Gly
        275                 280                 285

Thr Ser Ala Ala Pro Val Pro Ser Asp Asn His
    290                 295

<210> SEQ ID NO 15
<211> LENGTH: 299
<212> TYPE: PRT
<213> ORGANISM: Homo sapiens

<400> SEQUENCE: 15

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Cys
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Cys Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Ala Gln Ala Arg Leu Lys Ser Arg Phe Glu Pro Leu Ala Glu Asp Met
            260                 265                 270
```

```
Gln Arg Gln Trp Ala Gly Gln Val Glu Lys Val Gln Ala Ala Glu Gly
        275                 280                 285

Thr Ser Ala Ala Pro Val Pro Ser Asp Asn His
        290                 295

<210> SEQ ID NO 16
<211> LENGTH: 299
<212> TYPE: PRT
<213> ORGANISM: Homo sapiens

<400> SEQUENCE: 16

Lys Val Glu Gln Ala Val Glu Thr Glu Pro Glu Pro Glu Leu Arg Gln
1               5                   10                  15

Gln Thr Glu Trp Gln Ser Gly Gln Arg Trp Glu Leu Ala Leu Gly Arg
            20                  25                  30

Phe Trp Asp Tyr Leu Arg Trp Val Gln Thr Leu Ser Glu Gln Val Gln
        35                  40                  45

Glu Glu Leu Leu Ser Ser Gln Val Thr Gln Glu Leu Arg Ala Leu Met
    50                  55                  60

Asp Glu Thr Met Lys Glu Leu Lys Ala Tyr Lys Ser Glu Leu Glu Glu
65                  70                  75                  80

Gln Leu Thr Pro Val Ala Glu Glu Thr Arg Ala Arg Leu Ser Lys Glu
                85                  90                  95

Leu Gln Ala Ala Gln Ala Arg Leu Gly Ala Asp Met Glu Asp Val Arg
            100                 105                 110

Gly Arg Leu Val Gln Tyr Arg Gly Glu Val Gln Ala Met Leu Gly Gln
        115                 120                 125

Ser Thr Glu Glu Leu Arg Val Arg Leu Ala Ser His Leu Arg Lys Leu
    130                 135                 140

Arg Lys Arg Leu Leu Arg Asp Ala Asp Asp Leu Gln Lys Arg Leu Ala
145                 150                 155                 160

Val Tyr Gln Ala Gly Ala Arg Glu Gly Ala Glu Arg Gly Leu Ser Ala
                165                 170                 175

Ile Arg Glu Arg Leu Gly Pro Leu Val Glu Gln Gly Arg Val Arg Ala
            180                 185                 190

Ala Thr Val Gly Ser Leu Ala Gly Gln Pro Leu Gln Glu Arg Ala Gln
        195                 200                 205

Ala Trp Gly Glu Arg Leu Arg Ala Arg Met Glu Glu Met Gly Ser Arg
    210                 215                 220

Thr Arg Asp Arg Leu Asp Glu Val Lys Glu Gln Val Ala Glu Val Arg
225                 230                 235                 240

Ala Lys Leu Glu Glu Gln Ala Gln Gln Ile Arg Leu Gln Ala Glu Ala
                245                 250                 255

Ala Gln Ala Arg Leu Lys Ser Arg Phe Glu Pro Leu Ala Glu Asp Met
            260                 265                 270

Gln Arg Gln Trp Ala Gly Gln Val Glu Lys Val Gln Ala Ala Glu Gly
        275                 280                 285

Thr Ser Ala Ala Pro Val Pro Ser Asp Asn His
        290                 295

<210> SEQ ID NO 17
<211> LENGTH: 9
<212> TYPE: PRT
<213> ORGANISM: Artificial
<220> FEATURE:
<223> OTHER INFORMATION: ApoE mimetic anti-inflammatory peptide sequence
```

```
<220> FEATURE:
<221> NAME/KEY: MISC_FEATURE
<222> LOCATION: (1)..(1)
<223> OTHER INFORMATION: Xaa can be an amino acid having a hydrophobic
      side chain or an amino acid having a positively charged side chain
<220> FEATURE:
<221> NAME/KEY: MISC_FEATURE
<222> LOCATION: (2)..(2)
<223> OTHER INFORMATION: Xaa can be an amino acid having a hydrophobic
      side chain, an amino acid having a positively charged side chain,
      or an amino acid having a polar uncharged side chain
<220> FEATURE:
<221> NAME/KEY: MISC_FEATURE
<222> LOCATION: (3)..(4)
<223> OTHER INFORMATION: Xaa can be an amino acid having a positively
      charged side chain
<220> FEATURE:
<221> NAME/KEY: MISC_FEATURE
<222> LOCATION: (5)..(5)
<223> OTHER INFORMATION: Xaa can be an amino acid having a hydrophobic
      side chain or an amino acid having a positively charged side chain
<220> FEATURE:
<221> NAME/KEY: MISC_FEATURE
<222> LOCATION: (6)..(9)
<223> OTHER INFORMATION: Xaa can be any amino acid and is optionally
      absent

<400> SEQUENCE: 17

Xaa Xaa Xaa Xaa Xaa Xaa Xaa Xaa Xaa
1               5

<210> SEQ ID NO 18
<211> LENGTH: 12
<212> TYPE: PRT
<213> ORGANISM: Artificial
<220> FEATURE:
<223> OTHER INFORMATION: ApoE mimetic peptide sequence

<400> SEQUENCE: 18

Ala Ser His Leu Arg Lys Leu Arg Lys Arg Leu Leu
1               5                   10

<210> SEQ ID NO 19
<211> LENGTH: 12
<212> TYPE: PRT
<213> ORGANISM: Artificial
<220> FEATURE:
<223> OTHER INFORMATION: ApoE mimetic peptide sequence

<400> SEQUENCE: 19

Leu Arg Val Arg Leu Ala Ser Leu Leu Arg Lys Leu
1               5                   10
```

PEPTIDES FOR SUPPRESSING INFLAMMATION

CROSS REFERENCE TO RELATED APPLICATIONS

This application is a 35 U.S.C. §371 national phase entry of PCT Application PCT/US2012/029392, filed Mar. 16, 2012, and published in English on Sep. 27, 2012, as International Publication No. WO 2012/129077, and which claims the benefit under 35 U.S.C. §119(e) of U.S. Provisional Patent Application Ser. No. 61/454,342, filed Mar. 18, 2011, the disclosure of each of which is incorporated herein by reference in its entirety.

FIELD

The disclosure relates to peptides, methods, and compositions for reducing or suppressing inflammation, reducing or suppressing neuroinflammation, and treating neurological conditions.

SEQUENCE LISTING

A Sequence Listing is provided with the filing of the application in electronic form only, and is incorporated herein by reference. The Sequence Listing, entitled 1175-2TS_ST25.txt, was generated on Sep. 24, 2013 and is 12,469 bytes in size.

BACKGROUND

Apolipoprotein E ("ApoE") is a 299 amino acid (34 kDa) glycoprotein, produced primarily in the liver and brain that exhibits multiple biological functions. First recognized for its role in cholesterol transport and metabolism, ApoE is present in very-low-density lipoprotein (VLDL) and high-density lipoprotein (HDL) complexes, and ApoE can bind the low-density lipoprotein (LDL) receptor, the LDL-receptor-related protein (LRP), and the VLDL receptor. Weisgraber, (1994) *Adv. Protein Chem.* 45:249-302. ApoE is also known to have immunomodulatory properties, Laskowitz, et al., (2001) *Exp. Neurol.* 167:74-85, and to play a role in neurological disease and brain injury response, Laskowitz and Vitek, (2007) *Pharmacogenomics* 8:959-69.

The tertiary structure of ApoE includes an amino-terminal region with a four-α-helix motif that includes a receptor-binding domain and a carboxy-terminal region that is largely responsible for lipid binding. The receptor-binding region of ApoE has been mapped to a helical domain at residues 130-150 of the mature full-length protein, and this region of ApoE governs its ability to suppress glial activation and CNS inflammation.

SUMMARY

In an aspect, the disclosure provides an isolated peptide of 5, 6, 7, 8, or 9 amino acid residues that comprises Formula I:

(SEQ ID NO: 1)
X1-X2-X3-X4-X5 or a salt thereof, wherein X1 is selected from an amino acid having a hydrophobic side chain or an amino acid having a positively charged side chain; X2 is selected from an amino acid having a hydrophobic side chain, an amino acid having a positively charged side chain, or an amino acid having a polar uncharged side chain; X3 is selected from an amino acid having a positively charged side chain; X4 is selected from an amino acid having a positively charged side chain; and X5 is selected from an amino acid having a hydrophobic side chain or an amino acid having a positively charged side chain. Some embodiments of this aspect provide for a peptide of Formula II:

(SEQ ID NO: 17)
X1-X2-X3-X4-X5-X6-X7-X8-X9;

wherein X1, X2, X3, X4, and X5 are as noted above, and each of X6, X7, X8, and X9 are independently selected from any amino acid, and are optionally absent.

In an aspect, the disclosure provides an isolated peptide of Formula I:

(SEQ ID NO: 1)
X1-X2-X3-X4-X5 or a salt thereof, wherein X1 is selected from an amino acid having a hydrophobic side chain or an amino acid having a positively charged side chain; X2 is selected from an amino acid having a hydrophobic side chain, an amino acid having a positively charged side chain, or an amino acid having a polar uncharged side chain; X3 is selected from an amino acid having a positively charged side chain; X4 is selected from an amino acid having a positively charged side chain; and X5 is selected from an amino acid having a hydrophobic side chain or an amino acid having a positively charged side chain.

In embodiments of this aspect, the disclosure provides a peptide, or a salt thereof, according to SEQ ID NO:1, wherein X1 is V or R; X2 is S, A, or H; X3 is K or R; X4 is K or R; and X5 is R, L, or K. In some embodiments of this aspect, the disclosure provides a peptide, or salt thereof, comprises VSRKR (SEQ ID NO:2), VSKRR (SEQ ID NO:3), VSRRR (SEQ ID NO:4), VARKL (SEQ ID NO:5), RHKKL (SEQ ID NO:6), RARRL (SEQ ID NO:7), RSKKL (SEQ ID NO:8), RHKRR (SEQ ID NO:9), VARRL (SEQ ID NO:10), VARRK (SEQ ID NO:11), or RSKRR (SEQ ID NO:12).

In an aspect, the disclosure provides for compositions comprising the isolated peptide of Formula I, and a carrier, diluent, vehicle, or adjuvant. Embodiments of this aspect provide for a composition comprising a peptide, or a salt thereof, according to SEQ ID NO:1, wherein X1 is V or R; X2 is S, A, or H; X3 is K or R; X4 is K or R; and X5 is R, L, or K. In some embodiments of this aspect, the disclosure provides a composition comprising a peptide, or salt thereof, of VSRKR (SEQ ID NO:2), VSKRR (SEQ ID NO:3), VSRRR (SEQ ID NO:4), VARKL (SEQ ID NO:5), RHKKL (SEQ ID NO:6), RARRL (SEQ ID NO:7), RSKKL (SEQ ID NO:8), RHKRR (SEQ ID NO:9), VARRL (SEQ ID NO:10), VARRK (SEQ ID NO:11), or RSKRR (SEQ ID NO:12).

In an aspect, the disclosure provides a method of reducing inflammation in a subject in need thereof, the method comprising administering to the subject an effective amount of a peptide of Formula I:

(SEQ ID NO: 1)
X1-X2-X3-X4-X5 or a salt thereof, wherein X1 is selected from an amino acid having a hydrophobic side chain or an amino acid having a positively charged side chain; X2 is selected from an amino acid having a hydrophobic side chain, an amino acid having a positively charged side chain, or an amino acid having a polar uncharged side chain; X3 is selected from an amino acid having a positively charged side chain; X4 is selected from an amino acid having a positively charged side chain; and X5 is selected from an amino acid having a hydrophobic side chain or an amino acid having a positively charged side chain.

In embodiments of this aspect, the method comprises a peptide or a salt thereof according to SEQ ID NO:1, wherein X1 is V or R; X2 is S, A, or H; X3 is K or R; X4 is K or R; and X5 is R, L, or K. In some embodiments of this aspect, the method provides a peptide, or salt thereof, comprising VSRKR (SEQ ID NO:2), VSKRR (SEQ ID NO:3), VSRRR (SEQ ID NO:4), VARKL (SEQ ID NO:5), RHKKL (SEQ ID NO:6), RARRL (SEQ ID NO:7), RSKKL (SEQ ID NO:8), RHKRR (SEQ ID NO:9), VARRL (SEQ ID NO:10), VARRK (SEQ ID NO:11), or RSKRR (SEQ ID NO:12).

In an aspect, the disclosure provides a method of treating a neurological condition in a subject in need thereof, the method comprising administering to the subject an effective amount of a peptide of Formula I:

$$X1-X2-X3-X4-X5 \quad \text{(SEQ ID NO: 1)}$$

or a salt thereof, wherein X1 is selected from an amino acid having a hydrophobic side chain or an amino acid having a positively charged side chain; X2 is selected from an amino acid having a hydrophobic side chain, an amino acid having a positively charged side chain, or an amino acid having a polar uncharged side chain; X3 is selected from an amino acid having a positively charged side chain; X4 is selected from an amino acid having a positively charged side chain; and X5 is selected from an amino acid having a hydrophobic side chain or an amino acid having a positively charged side chain.

In embodiments of this aspect, the method comprises a peptide or a salt thereof according to SEQ ID NO:1, wherein X1 is V or R; X2 is S, A, or H; X3 is K or R; X4 is K or R; and X5 is R, L, or K. In some embodiments of this aspect, the method provides a peptide, or salt thereof, comprising VSRKR (SEQ ID NO:2), VSKRR (SEQ ID NO:3), VSRRR (SEQ ID NO:4), VARKL (SEQ ID NO:5), RHKKL (SEQ ID NO:6), RARRL (SEQ ID NO:7), RSKKL (SEQ ID NO:8), RHKRR (SEQ ID NO:9), VARRL (SEQ ID NO:10), VARRK (SEQ ID NO:11), or RSKRR (SEQ ID NO:12). In some embodiments the method comprises treating a neurological condition selected from at least one of traumatic CNS injury, subarachnoid hemorrhage, intracranial hemorrhage, stroke, experimental allergic encephalomyelitis, multiple sclerosis, neuroinflammation, chronic neurological disease, ALS, dementia, neuropathy, epilepsy, Parkinson's disease, and Alzheimer's disease.

In other aspects the disclosure provides a medicament comprising at least one peptide of formula I, methods for the preparation of the medicament, and a method comprising administration of the medicament as described herein.

In various embodiments of the aspects discussed above, the disclosure relates to and provides for peptides that consist essentially of, or consist of, the recited sequences and formulae.

The disclosure provides for additional aspects and embodiments that will be apparent to one of ordinary skill in the art in light of the drawings and detailed description that follows.

BRIEF DESCRIPTION OF THE DRAWINGS

FIGS. 11A-11B depict the inhibition of microglial TNF-α secretion by VR-55 (SEQ ID NO: 4), VL-5-1 (SEQ ID NO: 5) and VL-5-3 (SEQ ID NO: 10).

FIGS. 12A-12B depict the vestibulomotor function of mice treated with peptide following modified middle cerebral artery occlusion.

DETAILED DESCRIPTION

Figure 1:
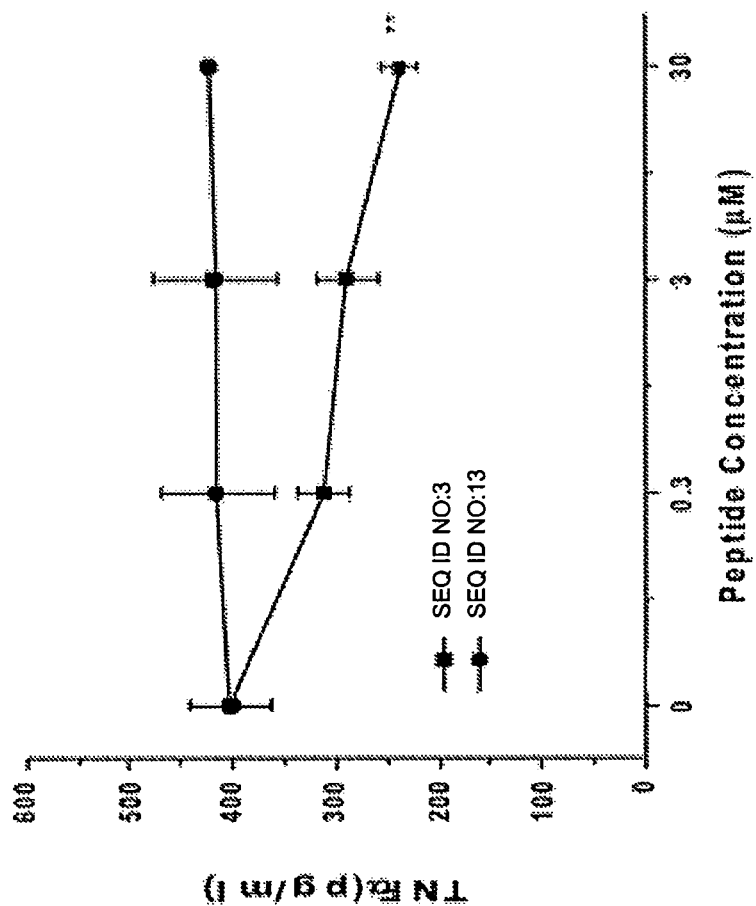
FIG. 1 depicts the inhibition of microglial TNF-α secretion by a peptide. Cultured BV-2 murine microglial cells were incubated with either the indicated concentrations of peptide (SEQ ID NO:3) or a negative control peptide (SEQ ID NO:13) and stimulated with lipopolysaccharide (LPS) (100 ng/mL) for six hours. After six hours, supernatants were harvested and the concentration of secreted TNF-α was measured by ELISA (** $p<0.01$; ANOVA).

It will be understood that the various aspects and embodiments described herein are merely intended to provide illustration and do not serve to limit the scope of the claims.

Articles "a" and "an" are used herein to refer to one or to more than one (i.e. at least one) of the grammatical object of the article. By way of example, "an element" means at least one element and can include more than one element. Unless otherwise defined, all technical terms used herein have the same meaning as commonly understood by one of ordinary skill in the art to which this disclosure belongs.

In a general sense the disclosure relates to peptides, including isolated and/or synthetic peptides that can exhibit ApoE activity (also referred to herein as "ApoE mimetic activity"). ApoE, as used herein, relates to any of the various isoforms (e.g., alleles) of the human apolipoprotein-E protein encoded by an APOE gene. Non-limiting examples of ApoE include ApoE3 (SEQ ID NO:14), ApoE2 (SEQ ID NO:15), and ApoE4 (SEQ ID NO:16). ApoE activity includes any functional biological activity, or combination of biological activities, that is associated with the ApoE protein, either in vitro or in vivo. ApoE activity can relate to, for example, any one or combination of cholesterol metabolism, binding to physiological ApoE receptor proteins; neuroprotective activity, antioxidant activity, anti-excitotic activities, modulation of glial cell activity, inflammation, modulation of neuroinflammation, and the like. Recent studies demonstrate that peptides having apoE mimetic activity can beneficial effect in a number of animal models including, for example, Alzheimer's disease (Laskowitz et al., (2010) *J Neurotrauma* 27:1983-1995); multiple sclerosis (Li et al., JPET, 2006); subarachnoid hemorrhage (Gao et al; 2006 Mesis et al., 2006); stroke (Tukhovskaya, J Neurosci Res, 2006), and neuropathy (Li et al., JPET, 2010). Thus, the peptides, compositions, and methods disclosed herein have broad applications as they can be used to treat a spectrum of diseases, disorders, and clinical indications associated with ApoE.

ApoE is a known ligand for receptors including scavenger receptors such as LDL receptor, VLDL receptor, LRP/α2M receptor, ER-2 receptor, LR8 receptor, ApoE receptor 2 (apoER2), and megalin/gp330 (collectively "ApoE receptors"). One region of ApoE known to participate in receptor-binding interactions is an α-helical domain that lies between residues 130-150 of the native ApoE polypeptide (SEQ ID NO:14). Active ApoE fragments that include this helical domain have shown ApoE mimetic activity (see U.S. Pat. Nos. 7,319,092 and 7,205,280, hereby incorporated by reference in their entireties). These peptides retain the native ApoE primary amino acid sequence in the receptor binding helical domain and preserve the native α-helical secondary structure (Laskowitz, et al. (2001) *Exp. Neurol.* 167:74-85). The activity of these peptides has been shown to be dependent on the retention of the native α-helical secondary structure (Laskowitz, et al. (2006) *Acta Neurol. Scand.* 114 (Supp. 185):15-20). As described in more detail below, it has been surprisingly found that small peptides (e.g., 1, 2, 3, 4, 5, 6, 7, 8, or 9 amino acid residues in length) that have no primary sequence identity to ApoE are effective to modulate, induce, and/or mimic ApoE biological activity and can be used in the treatment of various diseases, disorders, or conditions that involve ApoE biological function.

A "peptide" as used herein refers to a compound that comprises at least single amino acid residue, or derivative thereof, or a compound that comprises at least one amino acid mimetic. Amino acids are well known in the art and include, for example, isoleucine, leucine, alanine, asparagine, glutamine, lysine, aspartic acid, glutamic acid, methionine, cysteine, phenylalanine, threonine, tryptophan, glycine, valine, proline, serine, tyrosine, arginine, histidine, norleucine, ornithine, taurine, selenocysteine, selenomethionine, lanthionine, 2-aminoisobutyric acid, dehydroalanine, hypusine, citrulline, 3-aminopropanoic acid, gamma-aminobutryic acid, nitroarginine, N-methylated leucine, homoarginine, dimethyl arginine, acetyl lysine, azalysine, pyrrolysine, and the like. An "amino acid side chain" refers to the various organic substituent groups that differentiate one amino acid from another. An amino acid having a hydrophobic side chain includes the non-limiting examples of alanine (A), isoleucine (I), leucine (L), methionine (M), phenylalanine (F), tryptophan (W), tyrosine (Y), and valine (V). An amino acid having a positively charged side chain, under typical physiological conditions, includes the non-limiting examples of arginine (R), histidine (H), and lysine (K). An amino acid having a negatively charged side chain, under typical physiological conditions, includes the non-limiting examples of aspartic acid (D) and glutamic acid (E). An amino acid having a polar uncharged side chain includes the non-limiting examples of serine (S), threonine (T), asparagine (N), and glutamine (Q). Given these non-limiting examples, one of skill in the art will appreciate and be able to determine the characteristics of other amino acid side chains (e.g., as hydrophobic, positively/negatively charged, polar uncharged, and the like) that are not explicitly exemplified above. A "derivative" of an amino acid side chain refers to an amino acid side chain that has been modified structurally (e.g., through chemical reaction to form new species, covalent linkage to another molecule, and the like). Some embodiments provide for a peptide comprising modifications including, but not limited to, glycosylation, side chain oxidation, acetylation, amidation, or phosphorylation, as long as the modification does not destroy the biological activity of the peptides as herein described. For example, in some embodiments, a peptide may be modified by N-terminal acetylation and/or C-terminal amidation.

An "amino acid mimetic" as used herein is meant to encompass peptidomimetics, peptoids (poly-N-substituted glycines) and β-peptides (i.e., peptides that comprise one or more amino acids residues having the amino group attached at the β-carbon rather than the α-carbon). Suitably, the amino acid mimetic comprises an altered chemical structure that is designed to adjust molecular properties favorably (e.g., stability, activity, reduced immunogenic response, solubility, etc.). Typically, the altered chemical structure is thought to not occur in nature (e.g., incorporating modified backbones, non-natural amino acids, etc.). Thus, non-limiting examples of amino acid mimetic include D-peptides, retro-peptides, retro-inverso peptides, β-peptides, peptoids, and compounds that include one or more D-amino acids, poly-N-substituted glycine, or β-amino acid, or any combination thereof.

Typically, a peptide comprises a sequence of at least 3 amino acids (amino acid residues) or amino acid mimetics.

Embodiments of the disclosure relate to small peptides of at least 1, 2, 3, 4, 5, 6, 7, 8, or 9 amino acid residues, mimetics, or combinations thereof. Some embodiments described herein provide for peptides of fewer than 9, 8, 7, 6, 5, 4, 3, or 2 amino acid residues and/or mimetics. Some embodiments relate to peptides that are 5 amino acids in length. The peptides described herein can be provided in a charged form, typically with a net positive charge, and can be generated and used as salts (e.g., alkali metal salts, basic or acidic addition salts). The selection and formation of such salts are within the ability of one skilled in the art. See, e.g., *Remington: The Science and Practice of Pharmacy*, 21$^{st}$ ed., Lippincott Williams & Wilkins, A Wolters Kluwer Company, Philadelphia, Pa. (2005).

Embodiments of the disclosure provide synthetic peptides with ApoE mimetic activity. Though they may exhibit ApoE mimetic activity, the disclosed peptides do not share primary protein sequence identity with the ApoE polypeptide (SEQ ID NO: 13). In other words, the disclosed peptide sequences do not appear in the primary amino acid sequence of an ApoE polypeptide, nor do they exhibit α-helical secondary structure analogous to the native ApoE receptor-binding domain. In an embodiment, the synthetic peptides are optionally isolated and/or purified to a single active species.

In an aspect of the disclosure, the peptide comprises Formula I:

X1-X2-X3-X4-X5 (SEQ ID NO: 1)

or a salt thereof, wherein X1 is selected from an amino acid having a hydrophobic side chain or an amino acid having a positively charged side chain; X2 is selected from an amino acid having a hydrophobic side chain, an amino acid having a positively charged side chain, or an amino acid having a polar uncharged side chain; X3 is selected from an amino acid having a positively charged side chain; X4 is selected from an amino acid having a positively charged side chain; and X5 is selected from an amino acid having a hydrophobic side chain or an amino acid having a positively charged side chain. Some embodiments provide a peptide wherein $X_1$ is V or R; $X_2$ is S, A, or H; $X_3$ is K or R; $X_4$ is K or R; and $X_5$ is R, L, or K.

Some embodiments of this aspect provide for a peptide of Formula II:

X1-X2-X3-X4-X5-X6-X7-X8-X9; (SEQ ID NO: 17)

wherein X1, X2, X3, X4, and X5 are as noted above, and each of X6, X7, X8, and X9 are independently selected from any amino acid, and are optionally absent. In such embodiments, the peptide of Formula II can include 5 amino acid residues, 6 amino acid residues, 7 amino acid residues, 8 amino acid residues, or 9 amino acid residues.

In another aspect the disclosure provides a peptide of Formula I:

X1-X2-X3-X4-X5 (SEQ ID NO: 1)

or a salt thereof, wherein X1 is selected from an amino acid having a hydrophobic side chain or an amino acid having a positively charged side chain; X2 is selected from an amino acid having a hydrophobic side chain, an amino acid having a positively charged side chain, or an amino acid having a polar uncharged side chain; X3 is selected from an amino acid having a positively charged side chain; X4 is selected from an amino acid having a positively charged side chain; and X5 is selected from an amino acid having a hydrophobic side chain or an amino acid having a positively charged side chain. Some embodiments provide a peptide wherein $X_1$ is V or R; $X_2$ is S, A, or H; $X_3$ is K or R; $X_4$ is K or R; and $X_5$ is R, L, or K.

A number of non-limiting embodiments of peptides according to Formula I are disclosed in Table 1. In some embodiments the peptide can comprise VSRKR (SEQ ID NO:2), VSKRR (SEQ ID NO:3), VSRRR (SEQ ID NO:4), VARKL (SEQ ID NO:5), RHKKL (SEQ ID NO:6), RARRL (SEQ ID NO:7), RSKKL (SEQ ID NO:8), RHKRR (SEQ ID NO:9), VARRL (SEQ ID NO:10), VARRK (SEQ ID NO:11), or RSKRR (SEQ ID NO:12). In some embodiments, the peptide according to Formula I is VSRKR (SEQ ID NO:2), VSKRR (SEQ ID NO:3), VSRRR (SEQ ID NO:4), VARKL (SEQ ID NO:5), RHKKL (SEQ ID NO:6), RARRL (SEQ ID NO:7), RSKKL (SEQ ID NO:8), RHKRR (SEQ ID NO:9), VARRL (SEQ ID NO:10), VARRK (SEQ ID NO:11), or RSKRR (SEQ ID NO:12).

In some embodiments of all the aspects described herein, the peptides consist essentially of the amino acid sequences and formulae disclosed herein. In some embodiments of the all aspects described herein, the peptides consist of the amino acid sequences and formulae disclosed herein.

TABLE 1

| Peptide | Sequence | | | | |
|---|---|---|---|---|---|
| SEQ ID NO: 1 | $X_1$ | $X_2$ | $X_3$ | $X_4$ | $X_5$ |
| SEQ ID NO: 2 | V | S | R | K | R |
| SEQ ID NO: 3 | V | S | K | R | R |
| SEQ ID NO: 4 | V | S | R | R | R |
| SEQ ID NO: 5 | V | A | R | K | L |
| SEQ ID NO: 6 | R | H | K | K | L |
| SEQ ID NO: 7 | R | A | R | R | L |
| SEQ ID NO: 8 | R | S | K | K | L |
| SEQ ID NO: 9 | R | H | K | R | R |
| SEQ ID NO: 10 | V | A | R | R | L |
| SEQ ID NO: 11 | V | A | R | R | K |
| SEQ ID NO: 12 | R | S | K | R | R |

In some embodiments, the peptides can exhibit at least one ApoE mimetic activity. In some embodiments, for example, the disclosed peptides can bind one or more physiological ApoE receptors such as, for example, cell-surface receptors expressed by glial cells, as well as receptors that function to suppress the neuronal cell death and calcium influx (excitotoxicity) associated with N-methyl-D-aspartate (NMDA) exposure; protect against LPS-induced production of TNF-α and IL-6 (e.g., in an in vivo sepsis model); prevent, treat, or slow inflammatory disorders such as atherosclerosis, arthritis, or inflammatory bowel disease; suppress glial or microglial activation; suppress macrophage activation; suppress lymphocyte activation; suppress inflammation; suppress CNS inflammation; treat neuropathy; and/or ameliorate neuronal injury in neurodegenerative disease (e.g., mild cognitive impairment, dementia, Parkinson's disease, or Alzheimer's disease) and/or acute CNS trauma (e.g., traumatic brain injury).

In some embodiments, the peptides will bind to a particular receptor with similar affinity as ApoE. In some embodiments, the peptides will bind to a particular receptor with similar affinity as the previously disclosed longer 20-amino acid ApoE mimetic peptide which binds macrophages with a dissociation constant ($K_d$) of approximately 50 nM (Misra et al., (2001) *J. Leukocyte Biol.* 70:677-683). For example, the peptide may bind to a receptor with a $K_d$ equal or less than about 100 µM, about 90 µM, about 80 µM, about 70 µM, about 60 µM, about 50 µM, about 40 µM, about 30 µM, about 20 µM, about 10 µM, about 5 µM, about 1 µM, about 100 nM, about 90 nM, about 80 nM, about 70 nM, about 60 nM, about 50 nM, about 40 nM, about 30 nM, about 20 nM, about 10 nM, about 5 nM, about 1 nM, about 100 pM, about 90 pM, about 80 pM, about 70 pM, about 60 pM, about 50 pM, about 40 pM, about 30 pM, about 20 pM, about 10 pM, about 5 pM, or about 1 pM. The peptide may bind to a receptor with a $K_d$ greater or equal than about 1 pM, about 5 pM, about 10 pM, about 20 pM, about 30 pM, about 40 pM, about 50 pM, about 60 pM, about 70 pM, about 80 pM, about 90 pM, about 100 pM, about 1 nM, about 5 nM, about 10 nM, about 20 nM, about 30 nM, about 40 nM, about 50 nM, about 60 nM, about 70 nM, about 80 nM, about 90 nM, about 100 nM, about 1 µM, about 5 µM, about 10 µM, about 20 µM, about 30 µM, about 40 µM, about 50 µM, about 60 µM, about 70 µM, about 80 µM, about 90 µM, or about 100 µM. The peptide may bind to a receptor with a $K_d$ in the range of about 1 pM to about 10 pM, about 5 pM to about 15 pM, about 10 pM to about 20 pM, about 20 pM to about 30 pM, about 30 pM to about 40 pM, about 40 pM to about 50 pM, about 50 pM to about 60 pM, about 60 pM to about 70 pM, about 70 pM to about 80 pM, about 80 pM to about 90 pM, about 90 pM to about 100 pM, about 100 pM to about 1 nM, about 1 nM to about 10 nM, about 5 nM to about 15 nM, about 10 nM to about 20 nM, about 20 nM to about 30 nM, about 30 nM to about 40 nM, about 40 nM to about 50 nM, about 50 nM to about 60 nM, about 60 nM to about 70 nM, about 70 nM to about 80 nM, about 80 nM to about 90 nM, about 90 nM to about 100 nM, about 100 nM to about 1 µM, about 1 µM to about 10 µM, about 5 µM to about 15 µM, about 10 µM to about 20 µM, about 20 µM to about 30 µM, about 30 µM to about 40 µM, about 40 µM to about 50 µM, about 50 µM to about 60 µM, about 60 µM to about 70 µM, about 70 µM to about 80 µM, about 80 µM to about 90 µM, about 90 µM to about 100 µM, about 100 µM to about 1 µM. For example, the peptide may bind to a macrophage with a $K_d$ less than or equal to about 100 µM, about 90 µM, about 80 µM, about 70 µM, about 60 µM, about 50 µM, about 40 µM, about 30 µM, about 20 µM, about 10 µM, about 5 µM, about 1 µM, about 100 nM, about 90 nM, about 80 nM, about 70 nM, about 60 nM, about 50 nM, about 40 nM, about 30 nM, about 20 nM, about 10 nM, about 5 nM, about 1 nM, about 100 pM, about 90 pM, about 80 pM, about 70 pM, about 60 pM, about 50 pM, about 40 pM, about 30 pM, about 20 pM, about 10 pM, about 5 pM, or about 1 pM.

The extent of binding to an ApoE receptor can be assessed using any technique known in the art such as, for example, typical binding assays (e.g., competitive binding assays), ELISA, functional assays (e.g., as illustrated in the Examples), and the like. In some embodiments, the size of the peptides can confer improved pharmacokinetics, facilitate crossing the blood-brain barrier, allow intranasal administration, reduce production costs, increase potency (e.g., on a per-gram basis), and/or reduce peptide immunogenicity.

The peptides can be produced using any means for making polypeptides known in the art, including, e.g., synthetic and recombinant methods. For example, in some embodiments the peptides can be synthesized using synthetic chemistry techniques such as solid-phase synthesis, Merrifield-type solid-phase synthesis, t-Boc solid-phase synthesis, Fmoc solid-phase synthesis, BOP solid-phase synthesis, and solution-phase synthesis. See, for example, Stewart and Young, *Solid Phase Peptide Synthesis*, $2^{nd}$ ed., (1984) Pierce Chem. Co., Rockford Ill.; *The Peptides: Analysis, Synthesis, Biology*, Gross and Meienhofer, Eds., vols. 1-2 (1980) Academic Press, New York; Bodansky, *Principles of Peptide Synthesis*, (1984) Springer-Verlag, Berlin. In other embodiments, the peptides can be produced, for example, by expressing the peptide from a nucleic acid encoding the peptide in a cell or in a cell-free system according to recombinant techniques familiar to those of skill in the art. See, e.g., Sambrook et al., *Molecular Cloning: A Laboratory Manual*, (2001) Cold Spring Harbor Laboratory Press, Cold Spring Harbor, N.Y.; Ausubel et al., *Current Protocols in Molecular Biology*, (2002) John Wiley & Sons, Somerset, N.J.; each of which are hereby incorporated by reference in their entireties. The peptides can incorporate any of the various modifications and protective groups described herein or otherwise known to those of skill in the art, such as, for example, those described in McOmie, *Protective Groups in Organic Chemistry*, (1973) Plenum Press, New York.

In some embodiments, the peptides can be designed to mimic physical, chemical, and/or structural features of the α-helical receptor-binding domain that lies between residues 130-150 of the native ApoE polypeptide (SEQ ID NO: 14). For example, in some embodiments the peptides can be designed to mimic physical, chemical, and/or structural features of the polar face that extends along an outer surface of the three-dimensional structure of the native ApoE receptor-binding helix using a "linear walk" peptide-design approach, in which the amino acid at each successive position in the peptide is selected by attempting to emulate one or more properties (e.g., relative size/steric hindrance, polar, non-polar, charged, uncharged, hydropathy index (e.g., hydrophobicity, hydrophilicity), acidic, basic, ability to form bonds (e.g., covalent bonds, hydrogen bonds, van der Waals interactions), etc.) of each successive residue exposed on the polar face of the native ApoE receptor-binding helix by each descending periodic turn of the helix. In some embodiments, the peptide may be designed based on the physical, chemical, and/or structural features of the ApoE-binding domain of one or more ApoE receptors. For example, for an ApoE receptor having a binding pocket or surface that interacts with ApoE in an intermolecular receptor-ligand binding interaction, the peptide may be designed to maximize predicted binding affinity between the peptide and the ApoE binding pocket/surface of the receptor by selecting peptide amino acid residues expected to exhibit binding interactions along the receptor's ApoE binding pocket/surface.

In an aspect, the disclosure provides a method of treating a neurological condition in a subject in need thereof, the method comprising administering to the subject an effective amount of a peptide of Formula I or Formula II, or a composition or formulation comprising an effective amount of a peptide of Formula I or Formula II, or a combination thereof.

In another aspect, the disclosure provides a method of reducing inflammation in a subject in need thereof, the method comprising administering to the subject an effective amount of a peptide of Formula I or Formula II, or a composition or formulation comprising an effective amount of a peptide of Formula I or Formula II, or a combination thereof.

In embodiments relating to the above described aspects, the peptides and/or compositions can be used to treat, ameliorate, or prevent certain signs, symptoms, and/or deleterious neurological effects of acute and/or chronic CNS injury. As used herein, acute CNS injury includes but is not limited to stroke (caused by thrombosis, embolism or vasoconstriction), closed head injury, traumatic brain injury, global cerebral ischemia (e.g., ischemia due to systemic hypotension of any cause, including cardiac infarction, cardiac arrhythmia, hemorrhagic shock, and post coronary artery bypass graft brain injury), ischemic stroke, global anoxia, focal ischemia, subarachnoid hemorrhage, and intracranial hemorrhage. Ischemic damage to the central nervous system may result from either global or focal ischemic conditions. Global ischemia occurs where blood flow to the entire brain ceases for a period of time, such as during cardiac arrest. Focal ischemia occurs when a portion of the brain is deprived of normal blood flow, such as during thromboembolytic occlusion of a cerebral vessel, traumatic head injury, edema and brain tumors. Much of the CNS damage due to cerebral ischemia occurs during the hours or even days following the ischemic condition, and is secondary to the release of cytotoxic products by damaged tissue. Chronic CNS injury includes but is not limited to Alzheimer's disease (AD), Parkinson's disease, epilepsy, and HIV-associated encephalopathy. The finding that ApoE peptides may suppress glial activation provides a role for disclosed methods, peptides, and compositions treating any neurological disease involving microglial activation. For example, microglia express markers of activation in AD, suggesting that crucial inflammatory events in AD involve microglia. Such activated microglia cluster near amyloid plaques. Microglia are also activated in epilepsy.

In some embodiments, the peptides and/or compositions can be used to prevent, treat, or ameliorate the clinical neurological signs and symptoms associated with inflammatory conditions affecting the nervous system (e.g., the CNS). Non-limiting examples include multiple sclerosis, vasculitis, acute disseminated encephalomyelitis, and Guillain-Barre syndrome. In this regard, the disclosed ApoE mimetic peptides can be used alone or in combination with other known anti-inflammatory drugs or cytokines to formulate pharmaceutical compositions for the treatment of CNS inflammatory conditions.

In some embodiments, the peptides and/or compositions can be used to prevent, treat, or ameliorate conditions associated with NMDA excitotoxicity. NMDA excitotoxicity has been associated with neurolathyrism, amyotrophic lateral sclerosis (ALS), schizophrenia, HIV dementia and encephalopy, Huntington's chorea, Parkinson's disease, bipolar disorder, multiple sclerosis in humans and experimental allergic encephalomyelitis (EAE) in animals, pain, depression, stroke, epilepsy, inherited d-2-hydroxyglutaric aciduria, AD, and traumatic brain injury. In some embodiments, the peptides and/or compositions can block NMDA receptor mediated excitotoxicity and provide neuroprotection. NMDA antagonists are also used in clinical anesthesia, and have been shown to inhibit chronic pain, drug tolerance, and alcohol dependency. Thus, in some embodiments, the disclosed methods, peptides, and compositions may be used as ingredients in anesthesia formulations and in combined therapeutic compositions containing other known compounds useful for treating the described conditions.

In some embodiments, the peptides and/or compositions can be used to protect against LPS-induced production of cytokines in sepsis. Intact ApoE has been shown to protect mice from bacterial LPS-induced lethality. Other possible sepsis co-therapies involve administering anti-inflammatory cytokines, including IL-10, transforming growth factor-beta, granulocyte colony-stimulating factor, IFN-phi, macrophage migration inhibitory factor and high mobility group 1 protein, and monoclonal antibodies, including anti-endotoxin antibodies, anti-tumor necrosis factor antibodies, and anti-CD14 antibodies. Thus, embodiments provide for the use of peptides alone or in combination with other known anti-inflammatory cytokines and antibodies in compositions and methods for treating sepsis.

The effect of the disclosed methods, peptides, and compositions may be assessed at the cellular or tissue level (e.g., histologically or morphometrically) or by assessing a subject's neurological status. The suppression or reduction of glial activation can be assessed by various methods as would be apparent to those in the art; one such method is to measure the production or presence of compounds that are known to be produced by activated glia, and compare such measurements to levels of the same compounds in control situations. Alternatively, the effects of the present methods and compounds in suppressing, reducing or preventing microglial activation may be assessed by comparing the signs and/or symptoms of CNS disease in treated and control subjects, where such signs and/or symptoms are associated with or secondary to activation of microglia.

Typically, the terms "treating" and "treatment" when used with reference to a disease or a subject in need of treatment includes, but is not limited to, halting or slowing of disease progression, remission of disease, prophylaxis or lessening of symptoms and/or clinical indications, reduction in disease and/or symptom severity, or reduction in disease length as compared to an untreated subject, and/or in the absence of treatment. In embodiments, the methods of treatment can abate or ameliorate one or more clinical indications of the particular disease being treated. Certain embodiments relating to methods of treating a disease or condition associated with an ApoE activity comprise administration of therapeutically effective amounts of a peptide of Formula I, or of Formula II, or one or more peptides selected from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, as well as pharmaceutical compositions thereof. In embodiments, the method of treating can relate to any method that prevents further progression of the disease and/or symptoms, slows or reduces the further progression of the disease and/or symptoms, or reverses the disease and/or clinical symptoms associated with ApoE activity.

Subjects to be treated by the methods described herein encompass mammalian subjects, including both human subjects and non-human (animal) subjects such as dogs, cats, rabbits, goats, horses, pigs, cattle, etc. (including both male and female subjects and subjects of all ages including infant, juvenile, adolescent and adult subjects). Subjects may be treated for any purpose, such as for reducing inflammation, suppressing microglial activation, ameliorating chronic disease, etc. The term "concurrently administered" as used herein means that two compounds are administered sufficiently close in time to achieve a combined immunological effect. Concurrent administration may thus be carried out by sequential administration or simultaneous administration (e.g., simultaneous administration in a common, or the same, carrier).

In some embodiments, the disclosed peptides and compositions may be administered by any suitable route of administration, including, but not limited to, injection (subcutaneous, intraperitoneal, intravenous, intrathecal, intramuscular, intracerebroventricular, and spinal injection), intranasal, oral, transdermal, parenteral, inhalation, nasopharyngeal or transmucosal absorption. Administration encompasses the providing at least one peptide as described herein (e.g., of Formula I, Formula II, and/or SEQ ID NOs:1-12) formulated as a pharmaceutical composition. Administration of an active agent (e.g., compound, peptide, etc.) directly to the brain is known in the art. Intrathecal injection delivers agents directly to the brain ventricles and the spinal fluid. Surgically-implantable infusion pumps are available to provide sustained administration of agents directly into the spinal fluid. Spinal injection involves lumbar puncture with injection of a pharmaceutical compound into the cerebrospinal fluid. Administration also includes targeted delivery wherein peptide according to the disclosure is active only in a targeted region of the body (for example, in brain tissue), as well as sustained release formulations in which the peptide is released over a period of time in a controlled manner. Sustained release formulations and methods for targeted delivery are known in the art and include, for example, use of liposomes, drug loaded biodegradable microspheres, drug-polymer conjugates, drug-specific binding agent conjugates and the like. Pharmaceutically acceptable carriers are well known to those of skill in the art and include chitosan nanoparticles or other related enteric polymer formulations. Determination of particular pharmaceutical formulations and therapeutically effective amounts and dosing regimen for a given treatment is within the ability of one of skill in the art taking into consideration, for example, patient age, weight, sex, ethnicity, organ (e.g., liver and kidney) function, the extent of desired treatment, the stage and severity of the disease and associated symptoms, and the tolerance of the patient for the treatment.

Some embodiments of the methods described herein provide for intranasal delivery of one or more peptides described herein, or a composition comprising a peptide, for a subject having a chronic disease such as, for example multiple sclerosis, Alzheimer's disease, epilepsy, Parkinson's disease, arthritis, inflammatory bowel disease, leukemia, or atherosclerosis. Formulations and methods appropriate for intranasal and inhaled administration are known in the art.

In embodiments relating to therapeutic applications, the administration can be performed on a subject already suffering from the disorder of interest. Those in the incubation phase or the acute phase of the disease can be treated by the methods described herein, either alone or in conjunction with other treatments, as suitably based on the particular disease/condition, patient, and combination. One of skill in the art will be able to determine when a combination treatment is or is not suitable.

In therapeutic methods and uses, the peptides and composition described herein can be administered to a subject in an amount sufficient to treat, or at least partially arrest, symptoms and/or complications. An amount adequate to accomplish this is often referred to as "therapeutically effective dose." Amounts effective for this use will depend in part on the peptide, composition, the manner of administration, the stage and severity of the condition being treated, the age, weight, and general health of the patient, and the judgment of the prescribing physician.

In embodiments, effective amounts of the compositions and peptides disclosed herein can include less than about 100 mg/kg, less than about 50 mg/kg, less than about 25 mg/kg, less than about 10 mg/kg, less than about 1 mg/kg, less than about 0.1 mg/kg, less than about 0.05 mg/kg, less than about 0.01 mg/kg, less than about 0.005 mg/kg, and less than about 0.001 mg/kg peptide. In some embodiments, effective amounts of the compositions and peptides disclosed herein can include at least about 0.0001 mg/kg, at least about 0.001 mg/kg, at least about 0.005 mg/kg, at least about 0.01 mg/kg, at least about 0.05 mg/kg, at least about 0.1 mg/kg, at least about 0.5 mg/kg, at least about 1 mg/kg, at least about 5 mg/kg, and at least about 10 mg/kg peptide. This includes, for example, peptide amounts ranging from about 0.0001 mg/kg to about 100 mg/kg, from about 0.001 mg/kg to about 10 mg/kg, from about 0.005 mg/kg to about 0.5 mg/kg, and from about 0.01 mg/kg and about 0.05 mg/kg. In some embodiments, the methods, peptides, and compositions described herein can be employed in serious disease states, that is, life-threatening or potentially life threatening situations. In such cases, it is possible and may be felt desirable by the treating physician to administer substantial excesses of these compositions. Additionally, one of ordinary skill in the art would also know how to adjust or modify variables such as dosage, dosage schedules, and routes of administration, as appropriate, for a given subject.

The disclosed peptides and compositions may be administered acutely (i.e., during the onset or shortly after events leading to the condition requiring treatment), prophylactically (e.g., before scheduled surgery, or before the appearance of neurologic signs or symptoms), or during the course of a degenerative disease to reduce or ameliorate the progression of symptoms that would otherwise occur. The timing and interval of administration is varied according to the subject's symptoms, and may be administered at intervals spanning minutes, hours, or days, over a time course of hours, days, weeks or longer, as would be determined by one skilled in the art.

Some embodiments relating to pharmaceutical compositions for therapeutic or prophylactic treatment provide for formulations specific for any of mucosal (oral, nasal, inhalation, rectal, vaginal, tracheal, etc.), parenteral, topical, or local administration. For purposes herein, mucosal administration is different from topical administration, as mucosal administration refers to application of the vaccine to a mucosal surface such as a surface of the respiratory tract, gastrointestinal tract, reproductive tract, etc. In some embodiments, the pharmaceutical compositions are suitably administered parenterally, e.g., intravenously, subcutaneously, intradermally, or intramuscularly. Topical administration (i.e., non-mucosal) can be to a non-mucosal surface of a subject, such as the eye, ear, nails, hair, or skin, in any appropriate form such as aqueous or non-aqueous liquid (e.g., droplet), emulsion, paste, ointment, cream etc. Thus, the disclosure provides compositions for topical (mucosal or non-mucosal) or parenteral administration which comprise one or more small ApoE mimetic peptides, dissolved or suspended in an acceptable carrier, such as an aqueous carrier. In embodiments, the pharmaceutical composition is administered nasally. Any variety of aqueous carriers may be used, e.g., water, buffered water, 0.9% saline, 0.3% glycine, hyaluronic acid and the like. These compositions can be sterilized by conventional, well known sterilization techniques, or may be sterile filtered. The resulting solutions may be packaged for use as is, or lyophilized, the lyophilized preparation being combined with a sterile solution prior to administration. The compositions can contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc. Alternatively, the pharmaceutical compositions described herein can also be in dry powder formulations. In embodiments relating to dry powder vaccine formulations, typically the liquid vaccine is rapidly frozen and dried in a vacuum (e.g., freeze-dried) in the presence of at least one bulking agent (such as trehalose or other sugars) to provide a vaccine formulation that has superior temperature stability. Such dry powder vaccine formulations may be administered to the host as a dry powder, thereby eliminating the need for liquid reconstitution.

In aspects described herein that relate to compositions, including pharmaceutical compositions and formulations, some embodiments provide a composition that comprises at least one peptide according to SEQ ID NO:1 (e.g., SEQ ID NOs:1-12), in combination with an acceptable carrier, vehicle, diluent, or adjuvant. In further embodiments the composition comprises a peptide selected from any of SEQ ID NOs:2-12, or any combinations of two or more peptides thereof, in combination with a carrier, vehicle, diluent, or adjuvant.

In some embodiments, the disclosure provides a composition that consists essentially of a peptide of SEQ ID NO:1 or of SEQ ID NO:17 and a carrier, vehicle, diluent, or adjuvant. In further embodiments the composition consists essentially of a peptide selected from any of SEQ ID NOs:2-12, or any combinations of two or more peptides thereof, and a carrier, vehicle, diluent, or adjuvant.

In an aspect, the disclosure provides a medicament for treating a neurological condition in a subject in need thereof, wherein the medicament comprises an effective amount of a peptide of Formula I and/or Formula II.

In an aspect, the disclosure provides a medicament for treating inflammation in a subject in need thereof, wherein the medicament comprises an effective amount of a peptide of Formula I and/or Formula II.

While the following examples provide further detailed description of certain aspects and embodiments of the disclosure, they should be considered merely illustrative and not in any way limiting to the scope of the claims.

EXAMPLES

Example 1

Materials and Methods for Cell Culture-Based Assessment of Glial Activation In vitro methods have been developed using cultured cells for evaluating the ability of a compound, such as a peptide, to suppress glial activation. Laskowitz et al., (2001) *Exp. Neurol.*, 167:74-85. Glial cell cultures were grown and maintained under standard conditions. Cultured glial cells may include primary murine mixed glial cell cultures, murine BV-2 microglial cells, and human C3 microglial cells. Adherent glial cells were washed with OptiMEM® medium (available from Invitrogen Corp.) to remove serum and covered with fresh OptiMEM® medium containing peptide.

Peptides of 5 amino acids in length were applied to one or more samples of cells in parallel at concentrations ranging from about 0 to about 50 µM, such as 0.3, 3, and 30 µM. The peptides AL-10-1 (SEQ ID NO:18) and VL-17-9 (SEQ ID NO:19), which are longer peptides (12 amino acids each) were used as negative and positive controls, respectively. A series of peptides were screened in primary rat neuronal cortical culture exposed to NMDA using the method described in Aono et al., Neuroscience (2003) 116:437 and Aono et al., Neurobiology of Disease (2002) 11:214, both of which are incorporated by reference in their entirety (see Table 2). Neuroprotection from NMDA mediated cell death in primary neuronal culture was expressed as percentage decrease in LDH, 24 hours after exposure to NMDA compared to vehicle treated cultures (Table 2). LDH release is indicative of neuronal death after NMDA exposure. The peptide VR-55 (SEQ ID NO:4) reduced NMDA mediated excitotoxic cell death by approximately 19% at a concentration of 1 µM. Effects were specific, and not all peptides demonstrated neuroprotection. The positive control peptide VL-17-9 reduced LDH release by 31%. In comparison, the shorter VL-5-2 reduced LDH release by 31%, indicating that the shorter peptides also reduce NMDA mediated excitotoxic cell death.

TABLE 2

| | | 0.1 µM | 0.3 µM | 1 µM | 3 µM |
|---|---|---|---|---|---|
| VR-55 | Ac-VSRRR-NH2 (SEQ ID NO: 4) | −2.85% | 1.50% | 19.14% | 15.91% |
| VR-54 | Ac-VSKKR-NH2 (SEQ ID NO: 13) | | | −15.91% | |
| VR-53 | Ac-VSKRR-NH2 (SEQ ID NO: 3) | | | 7.03% | |
| VR-52 | Ac-VSRKR-NH2 (SEQ ID NO: 2) | | | 12.63% | |
| RL-5-3 | Ac-RSKKL-NH2 (SEQ ID NO: 8) | | | −20.80% | |
| RL-5-2 | Ac-RARRL-NH2 (SEQ ID NO: 7) | | | −5.23% | |
| RL-5-1 | Ac-RHKKL-NH2 (SEQ ID NO: 6) | | | −2.85% | |
| RR-5-2 | Ac-RSKRR-NH2 (SEQ ID NO: 12) | | | 0.08% | |
| RR-5-1 | Ac-RHKRR-NH2 (SEQ ID NO: 9) | | | 7.50% | |
| VL-5-3 | Ac-VARRL-NH2 (SEQ ID NO: 10) | −19.04% | −16.70% | 11.50% | |
| VL-5-2 | Ac-VARKL-NH2 (SEQ ID NO: 5) | | | 34.26% | |
| VL-5-1 | Ac-VARKL-NH2 (SEQ ID NO: 5) | 18.57% | 0.29% | 24.48% | |
| AL-10-1 | Ac-ASHLRKLRKRLL-NH2 (SEQ ID NO: 18) | | | −6.21% | |
| VL-17-9 | Ac-LRVRLASLLRKL-NH2 (SEQ ID NO: 19) | 16.19% | | 30.95% | |

Figure 6:
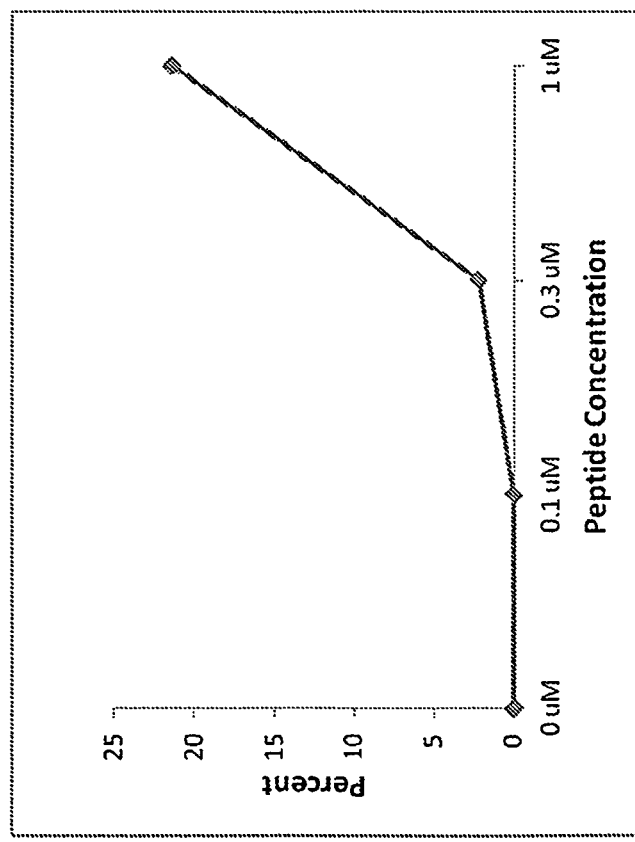
FIG. 6 depicts the percent suppression of LDH release after NMDA exposure in cultures treated with ApoE mimetic peptide (SEQ ID NO: 4).

Dose response of the neuroprotection from NMDA excitotoxicity in primary neuronal culture was determined for ApoE mimetic peptide VR-55 (SEQ ID NO: 4). FIG. 6 shows that the percent suppression of LDH release as a function of exposure to VR-55 (SEQ ID NO: 4) is dose dependent. Table 3 shows the cumulative data of all of the peptides in the related family that were screened in the same bioassay for their suppression capabilities, all at a concentration of 1 µM. "0" indicates less than 5% suppression; "+" indicates 5-10% suppression; "++" indicates 11-20% suppression; and "+++" indicates greater than 20% suppression. In addition to VL-17-9, several other candidates had greater than 20% suppression, including VR-55, VL-5-1, VL-5-2 and VR-52.

TABLE 3

List of ApoE mimetic peptides

| Peptide | 1 µM |
| --- | --- |
| VR-52 (SEQ ID NO: 2) | +++ |
| VR-53 (SEQ ID NO: 3) | + |
| VR-54 (SEQ ID NO: 13) | ++ |
| VR-55 (SEQ ID NO: 4) | +++ |
| RL-5-1 (SEQ ID NO: 6) | ++ |
| RL-5-2 (SEQ ID NO: 7) | 0 |
| RL-5-3 (SEQ ID NO: 8) | 0 |
| RR-5-1 (SEQ ID NO: 9) | + |
| RR-5-2 (SEQ ID NO: 12) | 0 |
| VL-5-1 (SEQ ID NO: 5) | +++ |
| VL-5-2 (SEQ ID NO: 5) | +++ |
| VL-5-3 (SEQ ID NO: 10) | ++ |
| AL-10-1 (SEQ ID NO: 18) | 0 |
| VL-17-9 (SEQ ID NO: 19) | +++ |

Larger peptides or proteins may need to be tested at higher concentrations to observe measurable suppression of glial activation. If using primary murine cells and BV-2 cells, cells are stimulated with 100 ng/ml *E. coli* LPS (available from Sigma-Aldrich Co.), and supernatant is collected six hours after LPS stimulation and assayed for nitrite (using a colorimetric Greiss reagent system, available from Promega Corp.) and/or TNF-α (using a solid-phase ELISA kit, available from Invitrogen Corp.). If using human C3 cells, cells are stimulated with 200 µg/ml polyinosinic acid 5' (available from Sigma-Aldrich Co.), and supernatant is collected 5 days after stimulation and assayed for TNF-α using a solid-phase ELISA kit (available from Invitrogen Corp.).

Example 2

Suppression of Microglial Activation by ApoE Mimetic Peptide

Murine BV-2 cultures were prepared and used to evaluate suppression of microglial activation as described in Example 1. Replicate samples of BV-2 cells were incubated without peptide, with an ApoE mimetic peptide (VSKRR; SEQ ID NO:3) at either 0.3 µM, 3 µM, or 30 µM, or with a negative control peptide (VSKKR; SEQ ID NO:13) at either 0.3 µM, 3 µM, or 30 µM. Each sample was stimulated with LPS and assessed for TNF-α production as described in Example 1. As depicted in FIG. 1, treatment with ApoE mimetic peptide (SEQ ID NO:3) at each dosage tested resulted in decreased TNF-α production relative to untreated cells or cells treated with negative control peptide (SEQ ID NO:13). The data indicate that peptides disclosed herein were useful in reducing the release of pro-inflammatory mediators.

The protective activity against brain injury-downregulating CNS inflammatory response was determined for ApoE mimetic peptides, VR-55 (SEQ ID NO: 4), VL-5-1 (SEQ ID NO: 5) and VL-5-3 (SEQ ID NO: 10). FIGS. 11A and 11B show that VR-55, VL-5-1, and VL-5-3 suppress the release of inflammatory cytokine TNF-α in mixed glial primary culture after exposure to LPS.

Example 3

Materials and Methods for Testing Neurological Deficits In Vivo

An experimental murine model for traumatic brain injury was developed. Laskowitz, et al. (2010) *J. Neurotrauma,* 27:1983-95. Male mice (age 12-14 weeks) were anesthetized with 4.3% isoflurane in oxygen in an anesthesia induction box for 90 seconds. The trachea was intubated and the lungs mechanically ventilated with 1.4% isoflurane in a 50/50 mixture of oxygen and nitrogen. Body temperature was maintained at 37° C. using surface heating/cooling. The top of the skull was exposed by a midline incision to identify anatomical landmarks, and a concave 3-mm metallic disc was secured to the skull surface with an adhesive, directly midline and just caudal to the bregma. The disc diffused the energy of impact and reduced the incidence of depressed skull fracture to less than 10%. After general anesthesia, mice were positioned in a stereotactic device and the skull was exposed. A pneumatic impactor (diameter: 2.0 mm; available from Air-Power, Inc.) discharged at 6.8±0.2 m/s with a head displacement of 3 mm was used to deliver a single midline impact to the disc surface.

An experimental murine model for intracerebral hemorrhage was also provided. James, et al. (2009) *Stroke,* 40:632-39. Male mice (age 16-20 weeks) were anesthetized with 4.6% isoflurane in oxygen in an anesthesia induction box for 90 seconds. The trachea was intubated and the lungs mechanically ventilated with 1.6% isoflurane in a 70/30 mixture of nitrogen/oxygen. Body temperature was maintained at 37° C. using an underbody warming system. The animal's head was secured in a stereotactic frame, local anesthetic was injected, and the scalp incised. After exposure of the skull, a burr hole was created 2 mm left lateral to bregma, and a 0.5 µL syringe needle (available from Hamilton Co.) was advanced to a depth of 3 mm from cortex. Type IV-S clostridial collagenase (available from Sigma-Aldrich Co.) was injected over a period of 5 minutes (0.1 U in 0.4 µL normal saline). The incision was then closed, and animals were allowed to recover spontaneous ventilation with subsequent extubation.

An experimental procedure for measuring neurological deficits was developed. An automated rotorod (available from Ugo Basile North America, Inc.) was used to assess vestibulomotor function. On the day before experimental induction of a neurological condition or injury (such as, for example, traumatic brain injury or intracerebral hemorrhage as described above), mice under went two consecutive conditioning trials at a set rotational speed (16 revolutions per minute) for 60 seconds followed by three additional trials with an accelerating rotational speed. The average time to fall from the rotating cylinder in the latter three trials was recorded as baseline latency. After injury, mice under went consecutive daily testing with three trials of accelerating rotational speed (intertribal interval of 15 minutes). Average latency to fall from the rod was recorded, and mice unable to grip the rod were scored with a latency of 0 seconds.

Another experimental procedure for measuring neurological deficits was developed using a Morris water maze. The procedure used a black aluminum pool containing a movable platform (7.5 cm diameter) and filled with 25-27° C. water opacified with powdered milk. Each training or testing session consisted of four trials per day with an interval of 20-30 minutes between trials. One day before testing, mice were trained using a visible platform (platform flagged and located in a different quadrant each trial to minimize quadrant habituation, no extra-maze visual cues) to habituate the mice to handling and swimming and to teach the mice the goal of the test—escaping the water by climbing on the platform. After the training day, mice were tested with a hidden platform submerged 1 cm below the water surface (four consecutive days, platform submerged in western quadrant for all trials with several extra-maze visual cues). For each test, mice were placed in the pool facing the perimeter and allowed to search for the platform for a maximum of 90 seconds. Mice were started in one of four different quadrants for each trial, with the starting quadrant order randomly defined each day. Latency to finding the platform and swimming speed were recorded using a computerized video tracking system (Ethovision 2.2.14; available from Noldus Information Technology, Leesburg Va.).

Example 4

Figure 2:
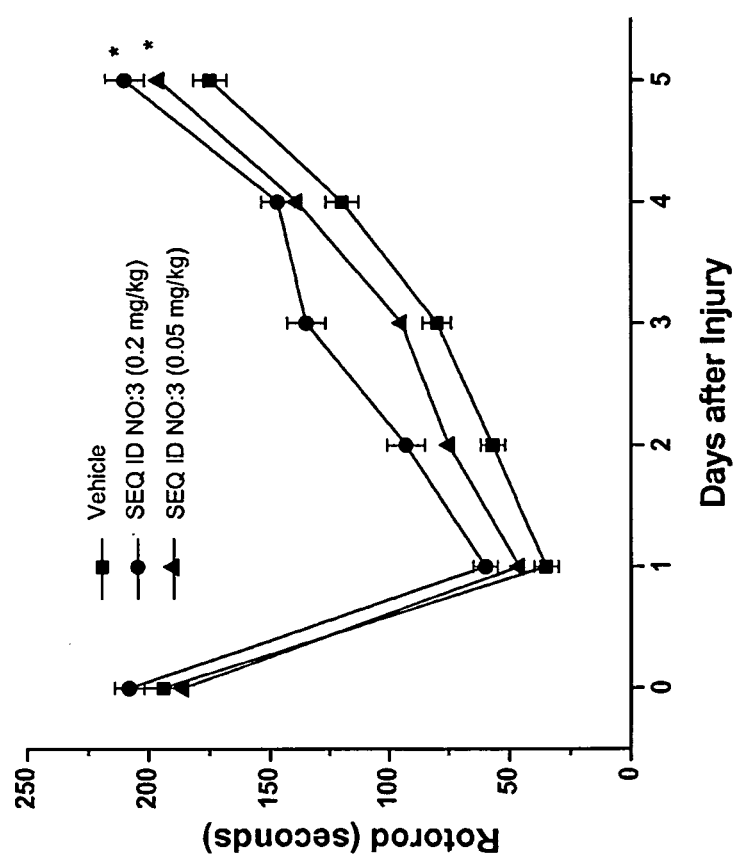
FIG. 2 depicts improved vestibulomotor function by mice treated with peptide following traumatic brain injury. Vestibulomotor function was assessed in terms of rotorod latency. Baseline rotorod latency was assessed before (Day 0) and each day following traumatic brain injury induced by a controlled pneumatic impact against the intact skull. At two hours and six hours after traumatic brain injury, mice received either peptide (SEQ ID NO:3; 0.05 mg/kg or 0.2 mg/kg) or saline vehicle by intravenous tail vein injection. Animals treated with peptide exhibited improved vestibulomotor performance relative to treatment with vehicle, as reflected by increased rotorod latency, throughout the testing period (* $p<0.05$; ANOVA).

Effect of ApoE Mimetic Peptide on Neurological Outcomes after Traumatic Brain Injury Groups of mice received either an ApoE mimetic peptide (SEQ ID NO:3; 0.05 mg/kg or 0.2 mg/kg) or carrier (saline) by intravenous tail vein injection at 2 hours and again at 6 hours after traumatic brain injury induced as described in Example 3. Each mouse was tested for vestibulomotor function by rotorod latency measured before and after injury, as described in Example 3. Animals treated with 0.05 mg/kg or 0.2 mg/kg ApoE mimetic peptide (SEQ ID NO:3) showed significantly improved vestibulomotor performance compared to carrier treatment as reflected by increased rotorod latency. See FIG. 2. The effect was durable through the five-day testing period. The data indicate that peptides disclosed herein are useful in treating traumatic brain injury.

Example 5

Figure 3:
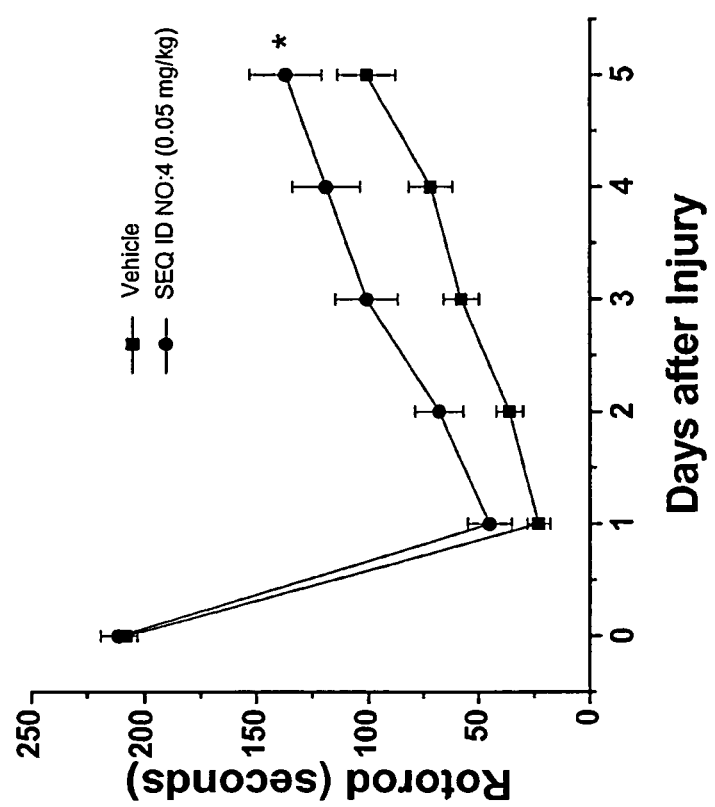
FIG. 3 depicts improved vestibulomotor function by mice treated with peptide following traumatic brain injury. Vestibulomotor function was assessed in terms of rotorod latency. Baseline rotorod latency was assessed before (Day 0) and each day following traumatic brain injury induced by a controlled pneumatic impact against the intact skull. At two hours and six hours after traumatic brain injury, mice received either peptide (SEQ ID NO:4; 0.05 mg/kg) or saline vehicle by intravenous tail vein injection. Animals treated with peptide exhibited improved vestibulomotor performance, as reflected by increased rotorod latency, throughout the testing period (* $p<0.05$; repeated measures ANOVA).
Figure 4:
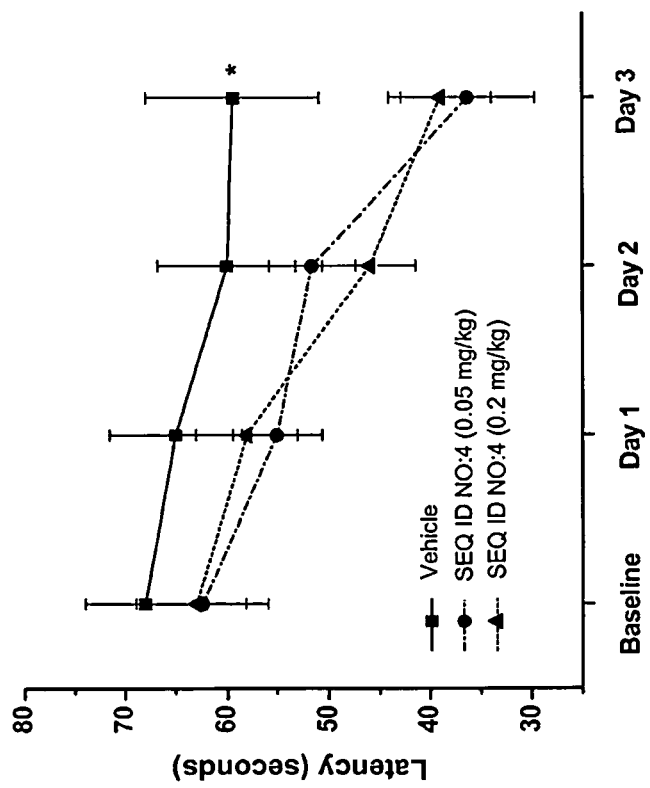
FIG. 4 depicts improved neurocognitive outcomes by mice treated with peptide following traumatic brain injury induced by a controlled pneumatic impact against the skull. At two hours and six hours after traumatic brain injury, mice received either peptide (SEQ ID NO:4, 0.05 mg/kg or 0.2 mg/kg) or saline vehicle by intravenous tail vein injection. Neurocognitive performance was assessed in terms of Morris water maze latency. Water maze latency was assessed by submerged platform testing starting on day 28 after traumatic brain injury, and performance was further evaluated on successive days 29, 30, and 31 post-injury. Animals treated with peptide exhibited improved neurocognitive outcomes, as reflected by decreased water maze latency, throughout the testing period (* $p<0.05$; ANOVA).

Effect of ApoE Mimetic Peptide on Neurological Outcomes after Traumatic Brain Injury Groups of mice received either an ApoE mimetic peptide (SEQ ID NO:4; 0.05 mg/kg) or carrier (saline) by intravenous tail vein injection at 2 hours and again at 6 hours after traumatic brain injury induced as described in Example 3. Each mouse was tested for vestibulomotor function by rotorod latency measured before and after injury, as described in Example 3. Animals treated with 0.05 mg/kg ApoE mimetic peptide (SEQ ID NO:4) had improved vestibulomotor performance as reflected by increased rotorod latency. See FIG. 3. The effect was durable through the five-day testing period. Other groups of mice received either an ApoE mimetic peptide (SEQ ID NO:4; 0.05 mg/kg or 0.2 mg/kg) or carrier (saline) by intravenous tail vein injection at 2 hours and again at 6 hours after traumatic brain injury induced as described in Example 3. Each mouse was tested for neurocognitive performance on days 28, 29, 30, and 31 post-injury using a Morris water maze as described in Example 3. Animals treated with ApoE mimetic peptide (SEQ ID NO:4) at either 0.05 mg/kg or 0.2 mg/kg exhibited improved neurocognitive outcomes as reflected by water maze latency. See FIG. 4. The data indicate that peptides disclosed herein are useful in treating traumatic brain injury.

Example 6

Figure 5:
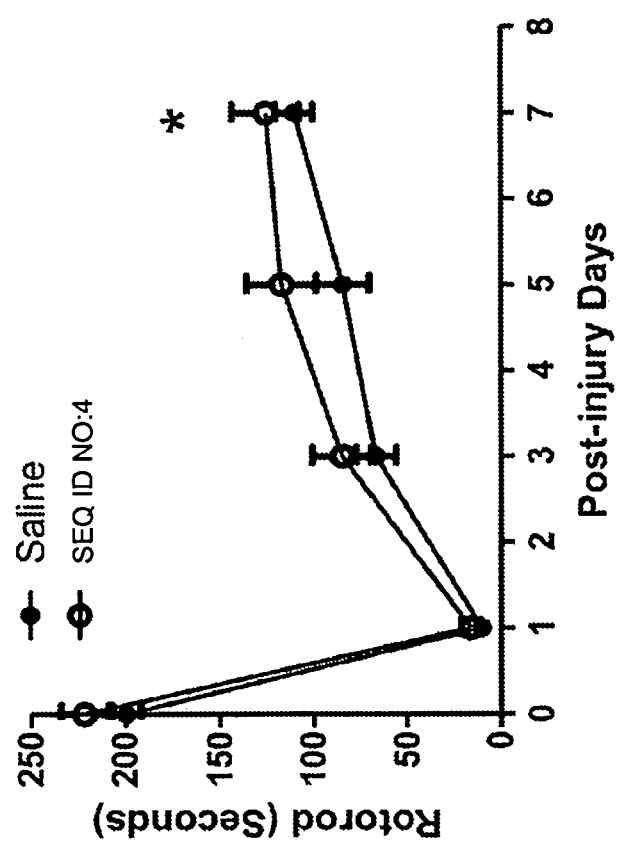
FIG. 5 depicts improved vestibulomotor function by mice treated with peptide following intracerebral hemorrhage. Vestibulomotor function was assessed in terms of rotorod latency. Baseline rotorod latency was assessed before (Day 0) and each day following intracerebral hemorrhage induced by stereotactic collagenase injection. At two hours and six hours after collagenase injection, mice received either peptide (SEQ ID NO:4; 0.05 mg/kg) or saline vehicle by intravenous tail vein injection. Animals treated with peptide exhibited improved vestibulomotor performance, as reflected by increased rotorod latency, throughout the testing period (* $p<0.05$; repeated measures ANOVA).

Effect of ApoE Mimetic Peptide on Neurological Outcomes after Intracerebral Hemorrhage Groups of mice received either an ApoE mimetic peptide (SEQ ID NO:4; 0.05 mg/kg) or carrier (saline) by intravenous tail vein injection a 2 hours and again at 6 hours after intracerebral hemorrhage induced as described in Example 3. Each mouse was tested for vestibulomotor function by rotorod latency measured before and after induced intracerebral hemorrhage as described in Example 3. Animals treated with 0.05 mg/kg ApoE mimetic peptide (SEQ ID NO:4) had improved vestibulomotor performance as reflected by increased rotorod latency. See FIG. 5. The effect was durable through the five-day testing period. The data indicate that peptides disclosed herein are useful in treating intracerebral hemorrhage.

Example 7

Effect of ApoE Mimetic Peptide on Neurological Outcomes after Blast Injury Data

A blast injury mouse study was performed using a shock tube blast model. A set of three shock tubes (FIG. 7A) was built to provide a range of blast conditions with realistic peak overpressure, scaled duration, and impulse. For peptide testing, the 1240 mm length, 78 mm diameter shock tube was used. The driver section was constant for all tests, and consisted of a 25 mm thick spacer flange bolted together with a corresponding blind flange and slip-on flange attached to the driven pipe. This driver section profile may be varied to change the overpressure characteristics of the tube. Full-faced gaskets (Graphite/Buna-N material) were installed between each flange to prevent leakage. The diaphragm was composed of a number of sheets of polyethylene terephthalate (PET) film installed between the driver spacer flange and the flange attached to the driven section. The driver section was filled with high-pressure helium through a fitting on the back of the blind flange until the diaphragm ruptured, sending the shock wave down the driven tube section.

Figure 7:
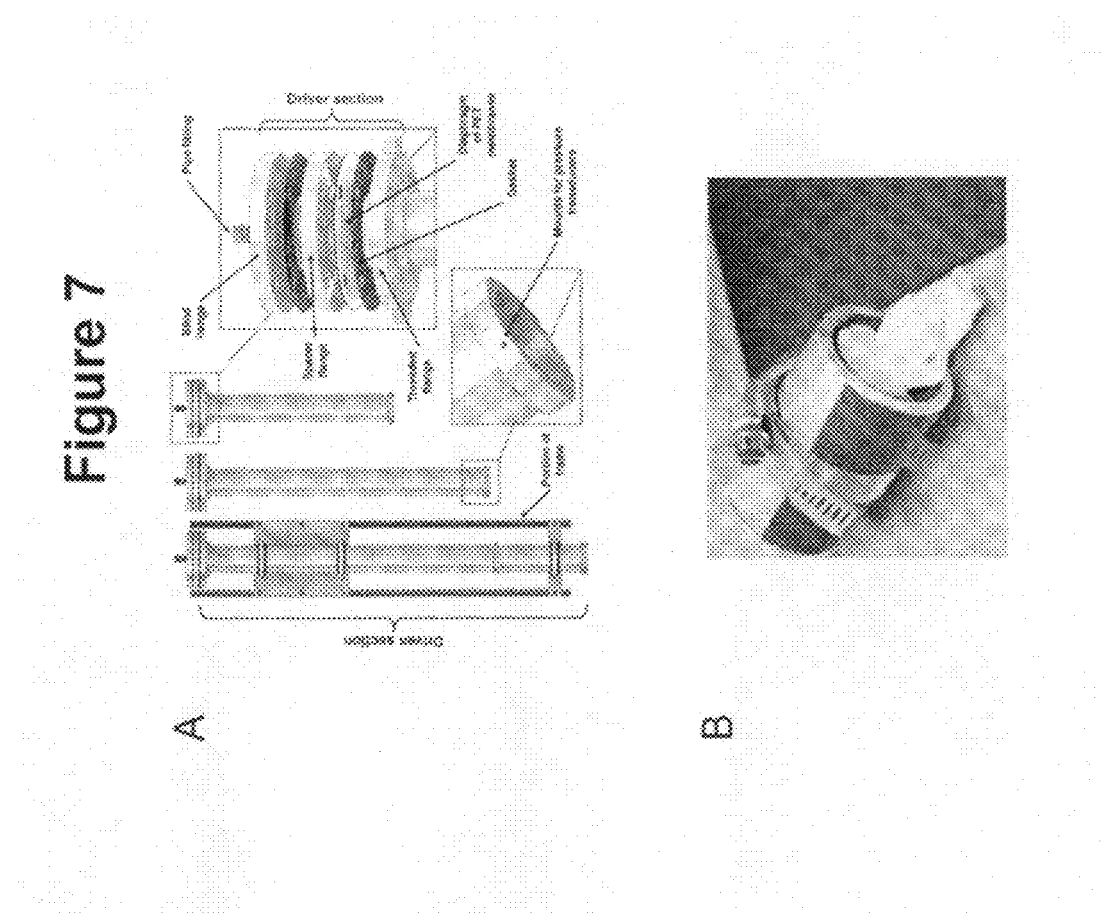
FIGS. 7A-7B depict sections of the shock tube blast model apparatus.

The shock tube was mounted vertically on an extruded aluminum frame using three vibration-damping U-bolts. Three flush-mounted piezoresistive pressure transducers (PT) (Endevco 8530B; Endevco Corp., San Juan Capistrano, Calif.) were spaced 120° around the diameter, offset 6 mm from the open end of the shock tube. Since the wall thickness of the tube was less than the length of the PT, a 6 mm thick collar (19 mm long) fit over the end of the tube and was welded in place to provide additional mounting support for the PTs. An additional PT was installed in the driver section to measure the burst pressure when the diaphragm ruptured. An aluminum fixture was used to provide thoracic protection for the mice (FIG. 7B). In previous testing, peak overpressure and impulse were decreased by more than a factor of 10. Peak incident overpressure, positive-phase duration, and peak incident impulse were recorded in the three end-tube PTs for each test (data not shown). The level of driver burst pressure was controlled using a range of diaphragm thicknesses (0.58 to 0.84 mm), and the driver gas tank pressure was regulated to 7.0 MPa. Atmospheric conditions (temperature, barometric pressure, humidity) were recorded prior to each test. All sensors were sampled at 1 MHz with a 500 kHz anti-aliasing filter. Data was post-processed using an $8^{th}$-order low-pass Butterworth filter with a cutoff frequency of 40 kHz.

Figure 8:
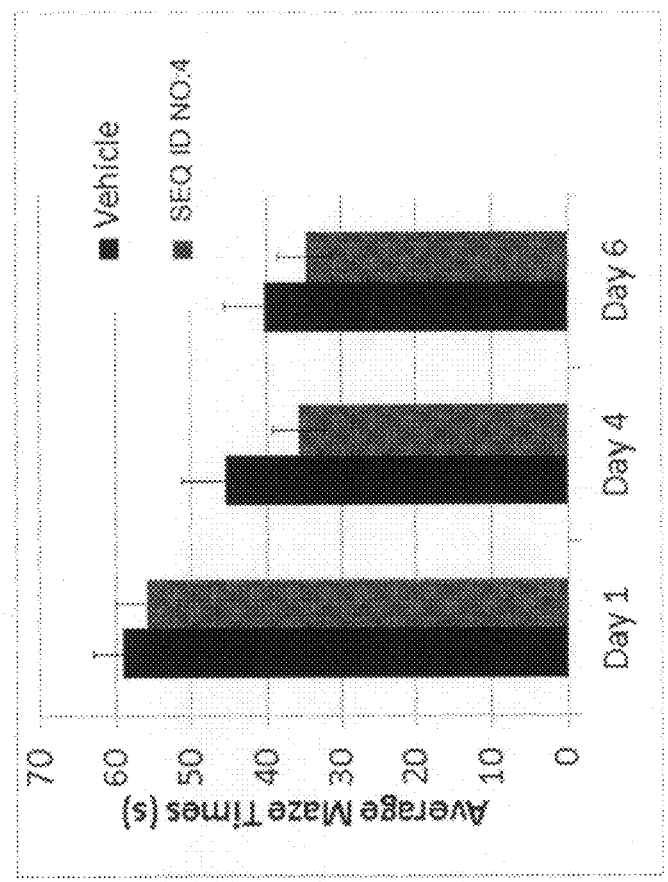
FIG. 8 depicts the efficacy of ApoE mimetic peptide (SEQ ID NO:4) on neurocognitive performance of mice with blast injury ($p=0.7$ on learning trend differences) in terms of Morris water maze latency.

Wild-type mice (Jackson Labs) were exposed to blast in two groups of 15, one with peptide injection (SEQ ID NO:4), and one with vehicle-only controls. The neurological deficits were measured in injured mice using the Morris water maze as described above. The efficacy of ApoE mimetic peptide on neurocognitive performance was examined in mice with blast injury as determined using the Morris water maze (FIG. 8). FIG. 8 shows that ApoE mimetic peptide reduces neurocognitive deficit after blast injury. Administration of the peptide resulted in a trend towards enhanced cognitive performance as demonstrated by increased time in the quadrant with the previously learned hidden platform (i.e., a probe trial to evaluate retention capabilities as described in Laskowitz et al., *J. Neurotrauma*, 24:1093-1107 (2007))(data not shown). Vehicle treated animals spent 17.8±1.9 seconds in the correct quadrant compared to the ApoE mimetic peptide (SEQ ID NO:4) treated animals which spent 21.8±2.7 seconds in the correct quadrant, p=0.24. The trend was towards improved learning in the Morris water maze (p=0.07). The trend was towards improved performance in the probe trial (p=0.25).

The mouse apnea data scales to other species and may be a good model system. The blast injury model was unique from the blunt injury model in the recovery of motor function and in the persistent and early cognitive deficits. With the rotorod results, the blast mice appeared to regain motor function quickly. There was no significant deficit between sham and injury condition post-blast. With the Morris water maze results, the blast mice showed significant cognitive deficits throughout the water maze trials.

Example 8

Pharmacokinetics in Blood and CNS for Intravenous Delivery

The amount of the ApoE mimetic peptide VSRRR (SEQ ID NO:4) in blood plasma and CNS was determined as follows:

VSRRR Quantitation in Mouse Plasma using LC/Selected Ion Monitoring (SIM)/MS

48 µL aliquots of mouse plasma were measured into the wells of a 2 mL 96-well plate. 6 µL of a stable isotope labeled (SIL) form of the VSRRR peptide ("VSRRR[10]"; SEQ ID NO:4) (5 picomoles/µL in 50 mM ammonium bicarbonate, pH 8, buffer) was added. 6 µL of a synthetic form of the VSRRR peptide ("VSRRR"; SEQ ID NO:4) in 50 mM Ammonium bicarbonate was added for standards and quality controls (QCs) and an equivalent volume of 50 mM ammonium bicarbonate was added to all wells containing mouse PK samples. 1140 µL of 50 mM ammonium formate, pH 10, was added for a final volume of 1200 mL. Salts and proteins were removed using OASIS® HLB Solid Phase Extraction (SPE) protocol as follows:

1. 500 µL methanol (MeOH) through each well×1.
2. 500 µL 25% acetonitrile (ACN)/1% trifluoroacetic acid (TFA)×1 (as pre-elution).
3. 500 µL MeOH×1
4. 500 µL 50 mM ammonium formate×2
5. 1 mL of each sample mixture was pipetted directly onto an OASIS® HLB plate (hydrophilic-lipophilic-balanced reversed-phase sorbent; Waters Corp.) into a corresponding well and slowly vacuumed through
6. 500 µL 50 mM ammonium formate×1
7. 500 µL 10% ACN/50 mM ammonium formate×2
8. 500 µL 25% ACN/50 mM ammonium formate×1
9. Removed plate collecting washes/flowthrough, and put in collection plate
10. Eluted with 100 µL 25% ACN/1% TFA×3, eluting with vacuum slowly. The final eluate should be approximately 300 µL.

The SPE eluate was dried using a vacuum centrifuge. The sample was reconstituted in 50 µL of buffer containing 1% acetonitrile (ACN), 0.1% trifluoroacetic acid (TFA), and 0.02% heptafluorobutyric acid (HFBA). Two microliters of reconstituted sample was analyzed by nanoscale capillary LC coupled to a high resolution, accurate mass tandem mass spectrometer. Specifically, the electrospray ionization source with NanoLockSpray™ (Waters Corp.) and nanoAcquity UPLC® system (Waters Corp.) were used with a nanoscale LC column (1.7 µm BEH130 C18 150 µm ID×100 mm long; Waters Corp.), 10-min gradient of 3% to 19% ACN with 0.1% formic acid (mobile phase A=0.1% formic acid/0.001% HFBA) with a total LC run time of 16.5 minutes, flow rate=1.8 µL/min and 35° C. column temperature. A SYNAPT™ G1 HDMS™ high resolution mass spectrometer (Waters Corp.) was used. Full Scan MS data was obtained over the mass region of 50-4000 Da using an Enhanced Duty Cycle scan function at 360 Da.

VSRRR and VSRRR[10] amounts were quantitated by measuring the area under the curve (AUC) of the Selected Ion Chromatograms of the doubly charged ions at high resolution (m/z 357.7 and 362.7). The final VSRRR quantitation amount was determined using the ratio of the AUCs (VSRRR/VSRRR[10]). The ratios from 5 animals were averaged per time point and calibration standards were used to generate a standard curve. Duplicate aliquots of QC samples were analyzed by LC/MS in triplicate to determine analytical reproducibility.

Figure 9:
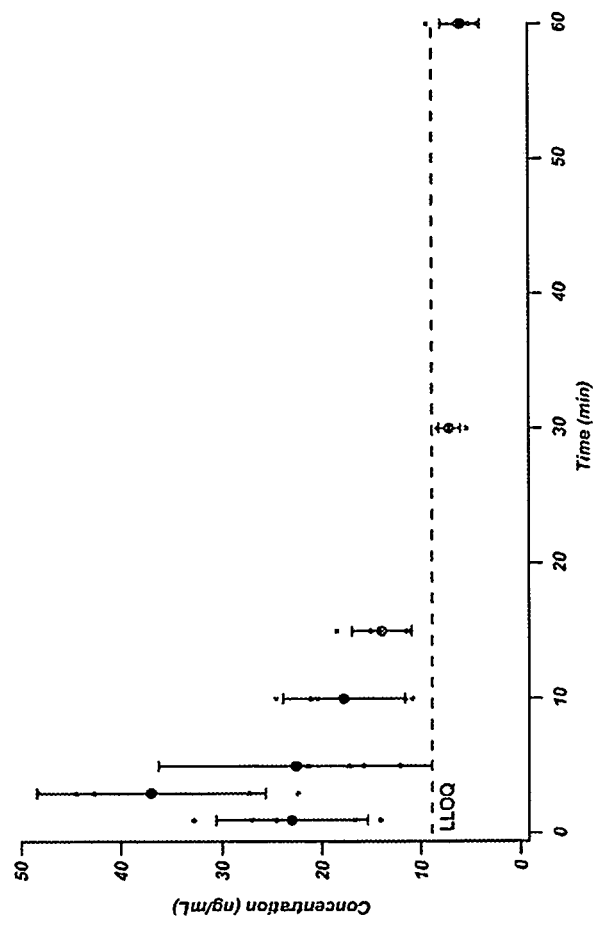
FIG. 9 depicts the average and individual amounts of VSRRR (SEQ ID NO:4) peptide in plasma of mice over time after a single dose of 0.8 mg/kg.

FIG. 9 shows the amount of peptide in the plasma sample over time after a single dosing of 0.8 mg/kg of the peptide. The lower level of quantitation (LLOQ) is indicated. Table 4 shows the results of intravenous (IV).

TABLE 4

| | IV | | | |
|---|---|---|---|---|
| Time Point (min) | Ratio Light/Heavy across 5 animals | Stdev across 5 animals | % CV across 5 animals | fmol/uL |
| 1 | 0.079 | 0.030 | 37.8 | 32.2 |
| 3 | 0.134 | 0.045 | 33.4 | 51.8 |
| 5 | 0.077 | 0.054 | 69.4 | 31.7 |
| 10 | 0.058 | 0.024 | 41.1 | 24.9 |
| 15 | 0.044 | 0.012 | 26.9 | 19.6 |
| 30 | 0.016 | 0.004 | 25.7 | 9.9 |
| 60 | 0.012 | 0.008 | 64.7 | 8.5 |

Mouse Brain PK on Therapeutic Peptide, VSRRR—Sample Preparation Procedure

Mice brains were weighed in a 1.5 mL Eppendorf tube. The entire brain was transferred to a 14 mL culture tube. 1 mL of 8 M urea in 50 mM ammonium formate (pH 10) with 2.5 pmol/mL SIL peptide per 100 mg wet tissue weight was added. For standard controls and QCs, 10 µL of peptide standard per every 100 mg of brain tissue (1%) was added with 990 µL of the aforementioned buffer to bring to a 1 mL total volume for every 100 mg of tissue. A tissue tearor was used on each sample for about 20 sec. 1.5 mL of the sample was transferred to a 2-mL Eppendorf tube. Each sample was probe sonicated for 3 bursts of 5 sec per burst. The sample was then heated at 37° C. for 30 min. The sample was centrifuged for 30 min at 15,000 rpm. Very little precipitate was visible at the bottom of each tube and avoided when pipetting 1 mL of the sample (out of 1.5 mL total volume) and placing directly onto an OASIS® plate. Salts and proteins were removed using the OASIS® HLB Solid Phase Extraction (SPE) protocol described above for the plasma sample. After the extraction, the samples were dried down in a Speed Vac and reconstitute in 25 μL of 1% ACN/0.1% TFA/0.02% HFBA. 3 μL of the sample was injected into a SYNAPT™ G2 HDMS™ (Waters Corp.) using Full Scan MS method, with a run time of 16.5 min total. Peptide(s) of interest were monitored between 3-8 min.

Figure 10:
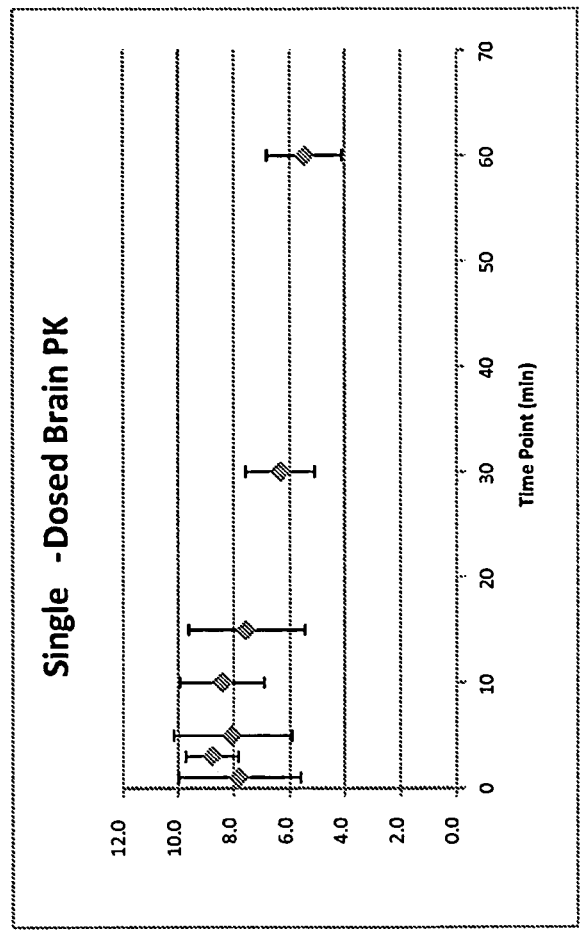
FIG. 10 depicts the CNS penetration of VSRRR (SEQ ID NO:4) peptide in brain tissue from mice over time.

Table 5 and FIG. 10 show the average amount of peptide in the CNS sample from 5 animals over time after a single dosing of 0.8 mg/kg of the peptide. FIG. 10 shows the lowest level of quantification at 1.4 pg/mg.

TABLE 5

Single-Dosed Brain PK

| Time Point (min) | fmol analyte/mg tissue | pg/mg of tissue | Std. Dev. (pg/mg) |
| --- | --- | --- | --- |
| 1 | 10.91 | 7.79 | 1.57 |
| 3 | 12.30 | 8.79 | 0.67 |
| 5 | 11.26 | 8.04 | 1.51 |
| 10 | 11.83 | 8.44 | 1.07 |
| 15 | 10.56 | 7.54 | 1.49 |
| 30 | 8.87 | 6.33 | 0.88 |
| 60 | 7.64 | 5.46 | 0.97 |

Table 6 shows the analyte concentration in 2×3-min brains and 2×10-min brains. The analyte concentrations were calculated from a single-point internal standard quantitation. The preliminary data suggest CNS penetration. The analyte concentrations were calculated from a 7-point standard curve calibration curve equation generated with samples between 1.4 pg analyte/mg tissue and 89.2 pg/mg (2× serial dilutions). The inter-animal reproducibility for the brain analyses is high (greater than 21% CV). The drug molecule in the single-dosed brain $C_{max}$ is about 9 pg analyte/mg tissue.

TABLE 6

Brain Pilot

| Sample ID | Mouse ID | Time Point (min) | Ratio to Heavy | fmol/mg (tissue) | pg/mg (tissue) |
| --- | --- | --- | --- | --- | --- |
| ID07386 | 11F63 | 3 | 0.245 | 15 | 11 |
| ID07387 | 11F64 | 3 | 0.371 | 23 | 17 |
| ID07388 | 11F67 | 10 | 0.157 | 10 | 7 |
| ID07389 | 11F68 | 10 | 0.435 | 27 | 19 |

Example 9

Effect of ApoE Mimetic Peptide in Murine Stroke Studies

Focal Ischemia-Reperfusion Model

A modified middle cerebral artery occlusion (MCAO) model (Huang et al., (1994) *Science*, 265:1883-1885; Laskowitz et al., (1997) *J. Cereb. Blood Flow Metab.*, 17:753-758) was used to determine the effect of the mimetic peptides on neurological function after stroke and to evaluate the peptide's efficacy as a therapeutic agent for stroke. The mice were endotracheally intubated after anesthesia induction with 4.6% isoflurane, and the lungs were mechanically ventilated with 1.6% isoflurane in 30% $O_2$/70% $N_2$. Via a midline cervical skin incision, the right common carotid artery was identified. The external carotid artery was ligated and transected. The internal carotid artery was dissected distally until the origin of the pterygopalatine artery was visualized. A 6-0 nylon monofilament with blunted tip lightly coated with silicone was inserted into the proximal external carotid artery stump and advanced 11 mm into the internal carotid artery to occlude the middle cerebral artery. After 90 min, the filament was removed to restore blood perfusion, and the skin incision closed with suture. Isoflurane was discontinued and the mice were extubated upon the recovery of spontaneous respiration. Post-injury mice were placed in an oxygen-enriched environment ($FIO_2$=50%) for 1 hr and then returned to their cages. Rectal temperature was continuously monitored and servo-regulated with surface heating/cooling at 37° C. throughout the procedure.

Testing of Motor Deficits

Two groups of 10-12 week old male C57Bl/6J mice, a control group (n=12) and a VR-55-treated group (n=9), received MCAO. The control group mice were given 100 μL sterile normal saline vehicle by intravenous tail vein injection at 30 min and 6 hrs after reperfusion injury, while the VR-55-treated group mice were given 100 μL sterile normal saline vehicle and VR-55 (SEQ ID NO: 4; 0.05 mg/kg) by intravenous tail vein injection at 30 min and 6 hrs after reperfusion injury.

An automated Rotorod (Ugo Basile, Comerio, Italy) was used to assess vestibulomotor function, as previously described above. On the day before MCAO, the mice underwent 2 consecutive conditioning trials at a set rotational speed (16 rpm) for 60 sec followed by 3 additional trials with an accelerating rotational speed. The average time to fall from the rotating cylinder in the latter 3 trials was recorded as baseline functional Rotorod latency. Starting from the first day after MCAO, mice underwent consecutive daily testing with 3 trials of accelerating rotational speed (intertrial interval of 15 min) for 3 days. The average latency to fall from the rod was recorded. Mice unable to grasp the rotating rod were assigned a latency of 0 sec.

As shown in FIGS. 12A and 12B, the control and VR-55-treated mice had similar baseline functional Rotorod latencies. The control mice had a baseline functional Rotorod latency of 217+/−20 sec ("Saline"), while the VR-55-treated mice had a baseline functional Rotorod latency of 214+/−22 sec ("VR-55"). At Day 1 post-injury, the control and VR-55-treated mice also had similar functional Rotorod latency. However, at Day 3 post-injury, the VR-55-treated mice showed an improvement in functional Rotorod latency compared to the control mice. The VR-55-treated mice had a functional Rotorod latency of 216+/−26 sec while the control mice had a functional Rotorod latency of 161+/−32 sec. These results are consistent with a reduction in delayed neuronal injury secondary to inflammatory response.

The treated mice are expected to show improved histological endpoints. The other mimetic peptides described herein will be administered in various dosages and are also expected to show improved functional and histological endpoints in an MCAO model of mouse stroke.

We claim:

1. An isolated pentapeptide of Formula I:

$$X1-X2-X3-X4-X5 \quad \text{(SEQ ID NO: 1)}$$

or a salt thereof, wherein
X1 is V;
X2 is S;
X3 is K or R;
X4 is K or R; and
X5 is R;
and wherein said pentapeptide is optionally N-terminal acetylated and/or C-terminal amidated.

2. The isolated pentapeptide of claim 1, wherein said pentapeptide is N-terminal acetylated and/or C-terminal amidated.

3. The pentapeptide of claim 2, wherein said pentapeptide is N-terminal acetylated and/or C-terminal amidated and has the amino acid sequence of VSRKR (SEQ ID NO:2), VSKRR (SEQ ID NO:3), or VSRRR (SEQ ID NO:4).

4. The pentapeptide of claim 1, wherein said pentapeptide is VSKRR (SEQ ID NO:3) modified by both N-terminal acetylation and C-terminal amidation.

5. The pentapeptide of claim 1, wherein said pentapeptide is VSRRR (SEQ ID NO: 4) modified by both N-terminal acetylation and C-terminal amidation.

6. A method of reducing inflammation in a subject in need thereof, the method comprising administering to the subject an effective amount of a pentapeptide of claim 1.

7. The method of claim 6, comprising administering the pentapeptide by an injection, inhalation, transdermal, intravenous, intranasal, intracranial, and/or intrathecal route.

8. A composition comprising the pentapeptide of claim 1 and a pharmaceutically acceptable carrier, vehicle, diluent, or adjuvant.

9. A composition comprising the pentapeptide of claim 2 and a pharmaceutically acceptable carrier, vehicle, diluent, or adjuvant.

10. A composition comprising the pentapeptide of claim 3 and a pharmaceutically acceptable carrier, vehicle, diluent, or adjuvant.

11. A composition comprising the pentapeptide of claim 4 and a pharmaceutically acceptable carrier, vehicle, diluent, or adjuvant.

12. A composition comprising the pentapeptide of claim 5 and a pharmaceutically acceptable carrier, vehicle, diluent, or adjuvant.

\* \* \* \* \*